United States Patent [19]

Gelfand et al.

[11] Patent Number: 4,889,818
[45] Date of Patent: Dec. 26, 1989

[54] PURIFIED THERMOSTABLE ENZYME

[75] Inventors: David H. Gelfand, Oakland; Susanne Stoffel, El Cerrito; Frances C. Lawyer, Oakland; Randall K. Saiki, Richmond, all of Calif.

[73] Assignee: Cetus Corporation, Emeryville, Calif.

[21] Appl. No.: 63,509

[22] Filed: Jun. 17, 1987

Related U.S. Application Data

[63] Continuation-in-part of Ser. No. 899,241, Aug. 22, 1986, abandoned.

[51] Int. Cl.$^4$ ............................................. C12N 9/00
[52] U.S. Cl. ..................................... 435/194; 135/183; 935/14
[58] Field of Search .................... 435/183, 194; 935/14

[56] References Cited

U.S. PATENT DOCUMENTS 4,683,194  7/1987  Saiki et al.
4,683,195  7/1987  Mullis et al.
4,683,202  7/1987  Mullis.

OTHER PUBLICATIONS

Kaboev et al., Jan. 1981, *J. Bact.* 145(1):21–26.
Stenesh and Roe, 1972, *Biochim. Biophys. Acta.*, 272:156–166.
Klimczak et al., 1986, *Biochem.* 25(17):4850–4855.
Rossi et al., 1986, *System. Appl. Microbiol.* 7:337–341.
Air et al., 1974, *FEBS (Feb. Eur. Biochem. Soc.) Lett.* 38(3):277–281.
Fabry et al., 1976, *Biochim. Biophys. Acta.* 453(3):228–235.
Kaledin et al., Sep. 1981, *Biokhimiya* 46(9):1576–1584 (Russian text), and *Biochem.* 46:1247–1254 (English text).
Kaledin et al., Nov. 1982, *Biokhimiya* 47(11):1785–1791 (Russian text), and *Biochem.* 47:1515–1521 (English text).
Ruttiman et al., 1985, *Eur. J. Biochem.* 149:41–46.
Kaledin et al., *Biokhimiya*, (1980) 45:644–651.
A. Chien et al., *J. Bacteriol.* (1976) 127:1550–1557.

*Primary Examiner*—Thomas G. Wiseman
*Assistant Examiner*—Patricia Carson
*Attorney, Agent, or Firm*—Janet E. Hasak; Kevin R. Kaster; Albert P. Halluin

[57] ABSTRACT

A purified thermostable enzyme is obtained that has unique characteristics. Preferably the enzyme is isolated from the *Thermus aquaticus* species and has a molecular weight of about 86,000–90,000 daltons. The thermostable enzyme may be native or recombinant and may be used in a temperature-cycling chain reaction wherein at least one nucleic acid sequence is amplified in quantity from an existing sequence with the aid of selected primers and nucleotide triphosphates. The enzyme is preferably stored in a buffer of non-ionic detergents that lends stability to the enzyme.

3 Claims, 2 Drawing Sheets

4,889,818

PURIFIED THERMOSTABLE ENZYME

CROSS-REFERENCE TO RELATED APPLICATION

This patent application is a continuation-in-part application of U.S. application Ser. No. 899,241, filed Aug. 22, 1986, now abandoned. This application is also related to copending U.S. application Ser. Nos. 899,344, filed Aug. 22, 1986, now abandoned which is a CIP of copending U.S. Ser. No. 839,331, filed Mar. 13, 1986, 899,061,filed Aug. 22, 1986, which is a CIP of copending U.S. Serial Nos. 833,368, filed Feb. 25, 1986; and 899,513, filed Aug. 22, 1986, which is a CIP of U.S. Pat. No. 4,683,195, filed Feb. 7, 1986, which is a CIP of U.S. Serial No. 824,044, filed Jan. 30, 1986, now abandoned, which is a divisional application of U.S. Pat. No. 4,683,202, filed Oct. 25, 1985, which is a CIP of U.S. Ser. No. 716,975, filed Mar. 28, 1985, now abandoned.

BACKGROUND OF THE INVENTION

1. Field of the Invention

The present invention relates to a purified thermostable enzyme. In one embodiment the enzyme is DNA polymerase purified from *Thermus aquaticus* and has a molecular weight of about 86,000–90,000.

2. Background Art

Extensive research has been conducted on the isolation of DNA polymerases from mesophilic microorganisms such as *E. coli*. See, for example, Bessman et al., *J. Biol. Chem.* (1957) 233:171-177 and Buttin and Kornberg (1966) *J. Biol. Chem.* 241:5419-5427.

In contrast, relatively little investigation has been made on the isolation and purification of DNA polymerases from thermophiles, such as *Thermus aquaticus*. Kaledin et al., *Biokhymiya* (1980) 45:644-651 discloses a six-step isolation and purification procedure of DNA polymerase from cells of *T. aquaticus* YT1 strain. These steps involve isolation of crude extract, DEAE-cellulose chromatography, fractionation on hydroxyapatite, fractionation on DEAE-cellulose, and chromatography on single-strand DNA-cellulose. The pools from each stage were not screened for contaminating endo- and exonuclease(s). The molecular weight of the purified enzyme is reported as 62,000 daltons per monomeric unit.

A second purification scheme for a polymerase from *T. aquaticus* is described by A. Chien et al., *J. Bacteriol.* (1976) 127:1550-1557. In this process, the crude extract is applied to a DEAE-Sephadex column. The dialyzed pooled fractions are then subjected to treatment on a phosphocellulose column. The pooled fractions are dialyzed and bovine serum albumin (BSA) is added to prevent loss of polymerase activity. The resulting mixture is loaded on a DNA-cellulose column. The pooled material from the column is dialyzed and analyzed by gel filtration to have a molecular weight of about 63,000 daltons, and, by sucrose gradient centrifugation of about 68,000 daltons.

The use of a thermostable enzyme to amplify existing nucleic acid sequences in amounts that are large compared to the amount initially present has been suggested in copending U.S. Pat. No. 4,683,195. Primers, nucleotide triphosphates, and a polymerase are used in the process, which involves denaturation, synthesis of template strands and hybridization. The extension product of each primer becomes a template for the production of the desired nucleic acid sequence. The application discloses that if the polymerase employed is a thermostable enzyme, it need not be added after every denaturation step, because the heat will not destroy its activity. No other advantages or details are provided on the use of a purified thermostable DNA polymerase. Furthermore, New England Biolabs had marketed a polymerase from *T. aquaticus*, but discovered that the polymerase activity decreased substantially with time in a storage buffer not containing non-ionic detergents.

Accordingly, there is a desire in the art to produce a purified, stable thermostable enzyme that may be used to improve the diagnostic amplification process described above.

SUMMARY OF THE INVENTION

Accordingly, the present invention provides a purified thermostable enzyme that catalyzes combination of nucleotide triphosphates to form a nucleic acid strand complementary to a nucleic acid template strand. Preferably the purified enzyme is DNA polymerase from *Thermus aquaticus* and has a molecular weight of about 86,000–90,000 daltons. This purified material may be used in a temperature-cycling amplification reaction wherein nucleic acid sequences are produced from a given nucleic acid sequence in amounts that are large compared to the amount initially present so that they can be detected easily.

The gene encoding the enzyme from DNA polymerase from *Thermus aquaticus* has also been identified and provides yet another means to retrieve the thermostable enzyme of the present invention. In addition to the gene encoding the approximately 86,000–90,000 dalton enzyme, gene derivatives encoding DNA polymerase activity are also presented.

Finally, the invention also encompasses a stable enzyme composition comprising a purified, thermostable enzyme as described above in a buffer containing one or more non-ionic polymeric detergents.

The purified enzyme, as well as the enzymes produced by recombinant DNA techniques, provide much more specificity than the Klenow fragment, which is not thermostable. In addition, the purified enzyme and the recombinantly produced enzymes exhibit the appropriate activity expected when dTTP or other nucleotide triphosphates are not present in the incubation mixture with the DNA template. Also, the enzymes herein have a broader pH profile than that of the thermostable enzyme from *Thermus aquaticus* described in the literature, with more than 50% of the activity at pH 7 as at pH 8. Finally, the thermostable enzyme herein can be stored in a buffer with non-ionic detergents so that it is stable, not losing activity over a period of time.

DESCRIPTION OF THE PREFERRED EMBODIMENTS

Figure 1:
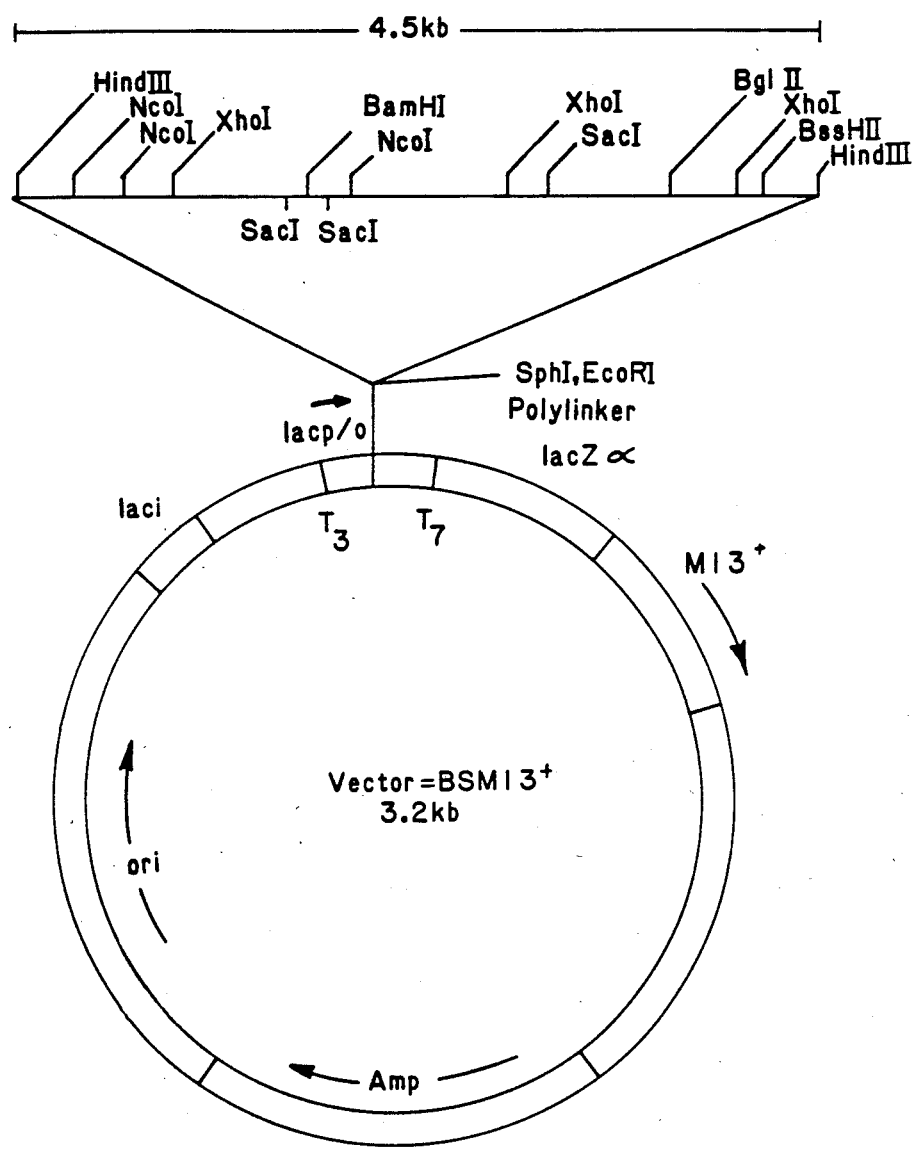
FIG. 1 is a restriction site map of plasmid pFC83 that contains the ~4.5 kb HindIII *T. aquaticus* DNA insert subcloned into plasmid BSM13+.
Figure 2:
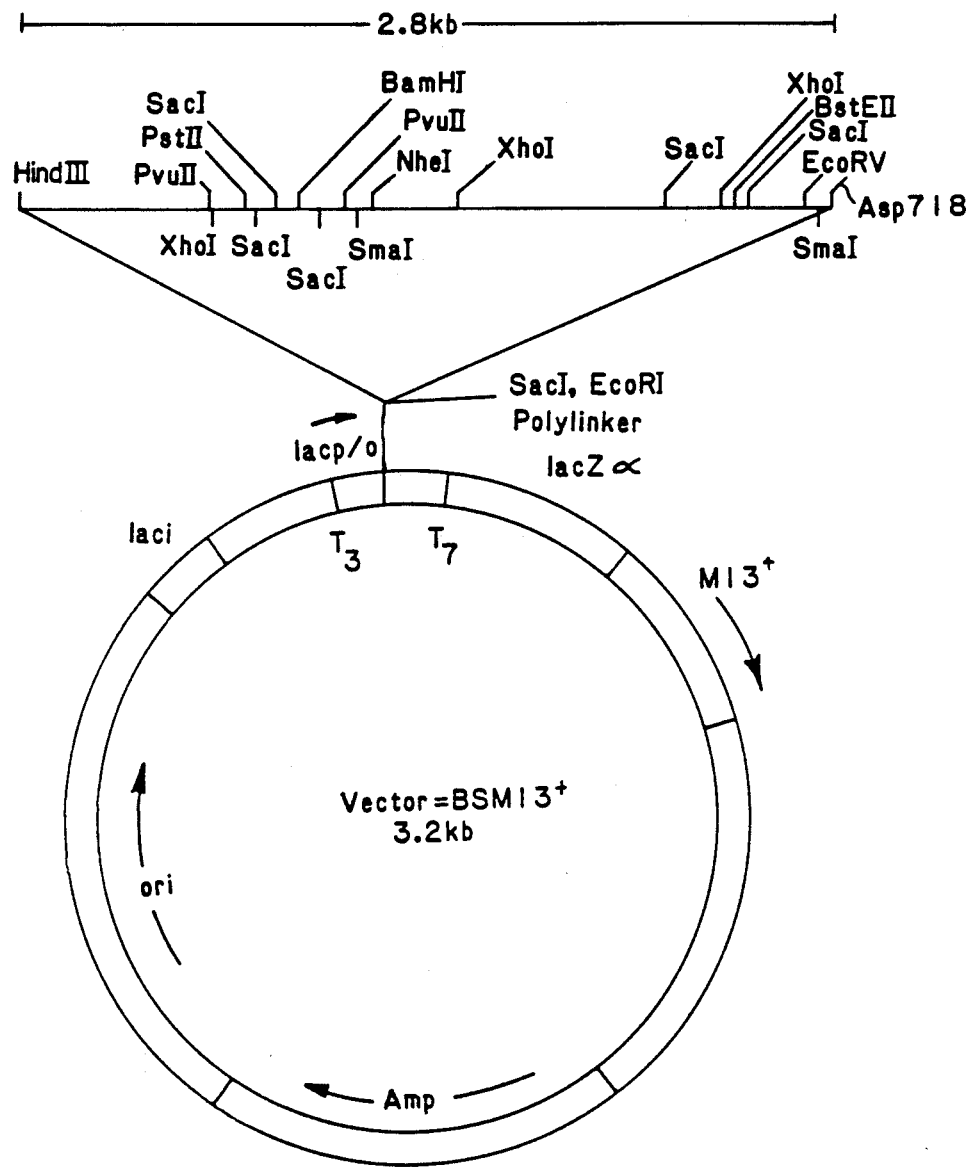
FIG. 2 is a restriction site map of plasmid pFC85 that contains the ~2.8 kb HindIII to Asp718 *T. aquaticus* DNA insert subcloned into plasmid BSM13+.

As used herein, "cell", "cell line", and "cell culture" can be used interchangeably and all such designations include progeny. Thus, the words "transformants" or "transformed cells" includes the primary subject cell and cultures derived therefrom without regard for the number of transfers. It is also understood that all progeny may not be precisely identical in DNA content, due to deliberate or inadvertent mutations. Mutant progeny that have the same functionality as screened for in the originally transformed cell are included.

The term "control sequences" refers to DNA sequences necessary for the expression of an operably linked coding sequence in a particular host organism. The control sequences that are suitable for procaryotes, for example, include a promoter, optionally an operator sequence, a ribosome binding site, and possibly, other as yet poorly understood sequences. Eucaryotic cells are known to utilize promoters, polyadenylation signals, and enhancers.

The term "expression system" refers to DNA sequences containing a desired coding sequence and control sequences in operable linkage, so that hosts transformed with these sequences are capable of producing the encoded proteins. In order to effect transformation, the expression system may be included on a vector; however, the relevant DNA may then also be integrated into the host chromosome.

The term "gene" as used herein refers to a DNA sequence that encodes a recoverable bioactive polypeptide or precursor. The polypeptide can be encoded by a full-length gene sequence or any portion of the coding sequence so long as the enzymatic activity is retained.

"Operably linked" refers to juxtaposition such that the normal function of the components can be performed. Thus, a coding sequence "operably linked" to control sequences refers to a configuration wherein the coding sequences can be expressed under the control of the sequences.

"Non-ionic polymeric detergents" refers to surface-active agents that have no ionic charge and that are characterized, for purposes of this invention, by their ability to stabilize the enzyme herein at a pH range of from about 3.5 to about 9.5, preferably from 4 to 8.5.

The term "oligonucleotide" as used herein is defined as a molecule comprised of two or more deoxyribonucleotides or ribonucleotides, preferably more than three. Its exact size will depend on many factors, which in turn depend on the ultimate function or use of the oligonucleotide. The oligonucleotide may be derived synthetically or by cloning.

The term "primer" as used herein refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, i.e., in the presence of four different nucleotide triphosphates and thermostable enzyme in an appropriate buffer ("buffer" includes pH, ionic strength, cofactors, etc.) and at a suitable temperature. For Taq polymerase the buffer herein preferably contains 1.5-2 mM of a magnesium salt, preferably $MgCl_2$, 150-200 $\mu M$ of each nucleotide, and 1 $\mu M$ of each primer, along with preferably 50 mM KCl, 10 mM Tris buffer, pH 8-8.4, and 100 $\mu g/ml$ gelatin.

The primer is preferably single-stranded for maximum efficiency in amplification, but may alternatively be double-stranded. If double-stranded, the primer is first treated to separate its strands before being used to prepare extension products. Preferably, the primer is an oligodeoxyribonucleotide. The primer must be sufficiently long to prime the synthesis of extension products in the presence of the thermostable enzyme. The exact lengths of the primers will depend on many factors, including temperature, source of primer and use of the method. For example, depending on the complexity of the target sequence, the oligonucleotide primer typically contains 15-25 nucleotides, although it may contain more or fewer nucleotides. Short primer molecules generally require cooler temperatures to form sufficiently stable hybrid complexes with template.

The primers herein are selected to be "substantially" complementary to the different strands of each specific sequence to be amplified. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to be amplified to hybridize therewith and thereby form a template for synthesis of the extension product of the other primer. However, for detection purposes, particularly using labeled sequence-specific probes, the primers typically have exact complementarity to obtain the best results.

As used herein, the terms "restriction endonucleases" and "restriction enzymes" refer to bacterial enzymes each of which cut double-stranded DNA at or near a specific nucleotide sequence.

As used herein, the term "thermostable enzyme" refers to an enzyme which is stable to heat and is heat-resistant and catalyzes (facilitates) combination of the nucleotides in the proper manner to form the primer extension products that are complementary to each nucleic acid strand. Generally, the synthesis will be initiated at the 3' end of each primer and will proceed in the 5' direction along the template strand, until synthesis terminates, producing molecules of different lengths. There may be a thermostable enzyme, however, which initiates synthesis at the 5' end and proceeds in the other direction, using the same process as described above.

The thermostable enzyme herein must satisfy a single criterion to be effective for the amplication reaction, i.e., the enzyme must not become irreversibly denatured (inactivated) when subjected to the elevated temperatures for the time necessary to effect denaturation of double-stranded nucleic acids. Irreversible denaturation for purposes herein refers to permanent and complete loss of enzymatic activity. The heating conditions necessary for denaturation will depend, e.g., on the buffer salt concentration and the length and nucleotide composition of the nucleic acids being denatured, but typically range from about 90 to about 105° C. for a time depending mainly on the temperature and the nucleic acid length, typically about 0.5 to four minutes. Higher temperatures may be tolerated as the buffer salt concentration and/or GC composition of the nucleic acid is increased. Preferably, the enzyme will not become irreversibly denatured at about 90-100° C.

The thermostable enzyme herein preferably has an optimum temperature at which it functions that is higher than about 40° C., which is the temperature below which hybridization of primer to template is promoted, although, depending on (1) magnesium and salt concentrations and (2) composition and length of primer, hybridization can occur at higher temperature (e.g., 45–70° C.). The higher the temperature optimum for the enzyme, the greater the specificity and/or selectivity of the primer-directed extension process. However, enzymes which are active below 40° C., e.g., at 37° C., are also within the scope of this invention provided they are heat-stable. Preferably, the optimum temperature ranges from about 50° to 90° C., more preferably 60–80° C.

The thermostable enzyme herein may be obtained from any source and may be a native or recombinant protein. Examples of enzymes that have been reported in the literature as being resistant to heat include heat-stable polymerases, such as, e.g., polymerases extracted from the thermophilic bacteria *Thermus flavus, Thermus ruber, Thermus thnrmophilus, Bacillus stearothermophilus* (which has a somewhat lower temperature optimum than the others listed), *Thermus aquaticus, Thermus lacteus, Thermus rubens,* and *Methanothermus fervidus.*

The preferred thermostable enzyme herein is a DNA polymerase isolated from *Thermus aquaticus.* Various strains thereof are available from the American Type Culture Collection, Rockville, Md., and are described by T. D. Brock, *J. Bact.* (1969) 98:289–297, and by T. Oshima, *Arch. Microbiol.* (1978) 117: 189–196. One of these preferred strains is strain YT-1.

For recovering the native protein the cells are grown using any suitable technique. One such technique is described by Kaledin et al., *Biokhimiya* (1980), supra, the disclosure of which is incorporated herein by reference. Briefly, the cells are grown on a medium, in one liter, of nitrilotriacetic acid (100 mg), tryptone (3 g), yeast extract (3 g), succinic acid (5 g), sodium sulfite (50 mg), riboflavin (1 mg), $K_2HPO_4$ (522 mg), $MgSO_4$(480 mg), $CaCl_2$ (222 mg), NaCl (20 mg), and trace elements. The pH of the medium is adjusted to 8.0±0.2 with KOH. The yield is increased if cultivated with vigorous aeration up to 20 g/liter of cells at a temperature of 70° C. Cells in the late logarithmic stage (determined by absorbance at 550 nm) are collected by centrifugation, washed with a buffer and stored frozen at −20° C.

In another method for growing the cells, described in Chien et al., *J. Bacteriol.* (1976), supra, the disclosure of which is incorporated herein by reference, a defined mineral salts medium containing 0.3% glutamic acid supplemented with 0.1 mg/l biotin, 0.1 mg/l thiamine, and 0.05 mg/l nicotinic acid is employed. The salts include nitrilotriacetic acid, $CaSO_4$, $MgSO_4$, NaCl, $KNO_3$, $NaNO_3$, $ZnSO_4$, $H_3BO_3$, $CuSO_4$, $NaMoO_4$, $CoCl_2$, $FeCl_3$, $MnSO_4$, and $Na_2HPO_4$. The pH of the medium is adjusted to 8.0 with NaOH.

In the Chien et al. technique, the cells are grown initially at 75° C. in a water bath shaker. On reaching a certain density, 1 liter of these cells is transferred to 16-liter carbons which are placed in hot-air incubators. Sterile air is bubbled through the cultures and the temperature maintained at 75° C. The cells are allowed to grow for 20 hours before being collected by centrifugation.

After cell growth, the isolation and purification of the enzyme take place in six stages, each of which is carried out at a temperature below room temperature, preferably about 4° C.

In the first stage or step, the cells, if frozen, are thawed, disintegrated by ultrasound, suspended in a buffer at about pH 7.5, and centrifuged.

In the second stage, the supernatant is collected and then fractionated by adding a salt such as dry ammonium sulfate. The appropriate fraction (typically 45–75% of saturation) is collected, dissolved in a 0.2M potassium phosphate buffer preferably at pH 6.5, and dialyzed against the same buffer.

The third step removes nucleic acids and some protein. The fraction from the second stage is applied to a DEAE-cellulose column equilibrated with the same buffer as used above. Then the column is washed with the same buffer and the flow-through protein-containing fractions, determined by absorbance at 280 nm, are collected and dialyzed against a 10 mM potassium phosphate buffer, preferably with the same ingredients as the first buffer, but at a pH of 7.5.

In the fourth step, the fraction so collected is applied to a hydroxyapatite column equilibrated with the buffer used for dialysis in the third step. The column is then washed and the enzyme eluted with a linear gradient of a buffer such as 0.01M to 0.5M potassium phosphate buffer at pH 7.5 containing 10 mM 2-mercaptoethanol and 5% glycerine. The pooled fractions containing thermostable enzyme (e.g., DNA polymerase) activity are dialyzed against the same buffer used for dialysis in the third step.

In the fifth stage, the dialyzed fraction is applied to a DEAE-cellulose column, equilibrated with the buffer used for dialysis in the third step. The column is then washed and the enzyme eluted with a linear gradient of a buffer such as 0.01 to 0.6M KCl in the buffer used for dialysis in the third step. Fractions with thermostable enzyme activity are then tested for contaminating deoxyribonucleases (endo- and exonucleasesl using any suitable procedure. For example, the endonuclease activity may be determined electrophoretically from the change in molecular weight of phage λ DNA or supercoiled plasmid DNA after incubation with an excess of DNA polymerase. Similarly, exonuclease activity may be determined electrophoretically from the change in molecular weight of DNA after treatment with a restriction enzyme that cleaves at several sites.

The fractions determined to have no deoxyribonuclease activity are pooled and dialyzed against the same buffer used in the third step.

In the sixth step, the pooled fractions are placed on a phosphocellulose column with a set bed volume. The column is washed and the enzyme eluted with a linear gradient of a buffer such as 0.01 to 0.4M KCl in a potassium phosphate buffer at pH 7.5. The pooled fractions having thermostable polymerase activity and no deoxyribonuclease activity are dialyzed against a buffer at pH 8.0.

The molecular weight of the dialyzed product may be determined by any technique, for example, by SDS PAGE using protein molecular weight markers. The molecular weight of one of the preferred enzymes herein, the DNA polymerase purified from *Thermus aquaticus,* is determined by the above method to be about 86,000–90,000 daltons.

The thermostable enzyme of this invention may also be produced by recombinant DNA techniques, as the gene encoding this enzyme has been cloned from *Thermus aquaticus* genomic DNA. The complete coding sequence for the *Thermus aquaticus* (Taq) polymerase can be derived from bacteriophage CH35:Taq#4-2 on an approximately 3.5 kilobase (kb) BglII-Asp718 (partial) restriction fragment contained within an ~18 kb genomic DNA insert fragment. This bacteriophage was deposited with the American Type Culture Collection (ATCC) on May 28, 1987 and has accession No. ATCC 40336. Alternatively, the gene can be constructed by ligating an ~750 base pair (bp) BglII-HindIII restriction fragment isolated from plasmid pFC83 (ATCC 67422 deposited May 28, 1987) to an ~2.8 kb HindIII-Asp718 restriction fragment isolated from plasmid pFC85 (ATCC 67421 deposited May 28, 1987). The pFC83 restriction fragment comprises the amino-terminus encoding region of the Taq polymerase gene while the restriction fragment from pFC85 comprises the carboxyl-terminus encoding region. Thus, ligation of these two fragments into a correspondingly digested vector with appropriate control sequences will result in the translation of a full-length Taq polymerase.

It has also been found that the entire coding sequence of the Taq polymerase gene is not required to recover a biologically active gene product with the desired enzymatic activity. Amino-terminal deletions wherein approximately one-third of the coding sequence is absent have resulted in producing a gene product that is quite active in polymerase assays.

In addition to the N-terminal deletions, individual amino acid residues in the peptide chain comprising Taq polymerase may be modified by oxidation, reduction, or other derivatization, and the protein may be cleaved to obtain fragments that retain activity. Such alterations that do not destroy activity do not remove the DNA sequence encoding such protein from the definition of gene.

Thus, modifications to the primary structure itself by deletion, addition, or alteration of the amino acids incorporated into the sequence during translation can be made without destroying the activity of the protein. Such substitutions or other alterations result in proteins having an amino acid sequence encoded by DNA falling within the contemplated scope of the present invention.

Polyclonal antiserum from rabbits immunized with the purified 86,000-90,000 dalton polymerase of this invention was used to probe a *Thermus aquaticus* partial genomic expression library to obtain the appropriate coding sequence as described below. The cloned genomic sequence can be expressed as a fusion polypeptide, expressed directly using its own control sequences, or expressed by constructions using control sequences appropriate to the particular host used for expression of the enzyme.

Of course, the availability of DNA encoding these sequences provides the opportunity to modify the codon sequence so as to generate mutein forms also having DNA polymerase activity.

Thus, these tools can provide the complete coding sequence for Taq DNA polymerase from which expression vectors applicable to a variety of host systems can be constructed and the coding sequence expressed. It is also evident from the foregoing that portions of the Taq polymerase-encoding sequence are useful as probes to retrieve other thermostable polymerase-encoding sequences in a variety of species. Accordingly, portions of the genomic DNA encoding at least six amino acids can be replicated in *E. coli* and the denatured forms used as probes or oligodeoxyribonucleotide probes can be synthesized which encode at least six amino acids and used to retrieve additional DNAs encoding a thermostable polymerase. Because there may not be a precisely exact match between the nucleotide sequence in the *Thermus aquaticus* form and that in the corresponding portion of other species, oligomers containing approximately 18 nucleotides (encoding the six amino acid stretch) are probably necessary to obtain hybridization under conditions of sufficient stringency to eliminate false positives. The sequences encoding six amino acids would supply information sufficient for such probes.

Suitable Hosts, Control Systems and Methods

In general terms, the production of a recombinant form of Taq polymerase typically involves the following:

First, a DNA is obtained that encodes the mature (used here to include all muteins) enzyme or a fusion of the Taq polymerase to an additional sequence that does not destroy its activity or to an additional sequence cleavable under controlled conditions (such as treatment with peptidase) to give an active protein. If the sequence is uninterrupted by introns it is suitable for expression in any host. This sequence should be in an excisable and recoverable form.

The excised or recovered coding sequence is then preferably placed in operable linkage with suitable control sequences in a replicable expression vector. The vector is used to transform a suitable host and the transformed host cultured under favorable conditions to effect the production of the recombinant Taq polymerase. Optionally the Taq polymerase is isolated from the medium or from the cells; recovery and purification of the protein may not be necessary in some instances, where some impurities may be tolerated.

Each of the foregoing steps can be done in a variety of ways. For example, the desired coding sequences may be obtained from genomic fragments and used directly in appropriate hosts. The constructions for expression vectors operable in a variety of hosts are made using appropriate replicons and control sequences, as set forth below. Suitable restriction sites can, if not normally available, be added to the ends of the coding sequence so as to provide an excisable gene to insert into these vectors.

The control sequences, expression vectors, and transformation methods are dependent on the type of host cell used to express the gene. Generally, procaryotic, yeast, insect or mammalian cells are presently useful as hosts. Procaryotic hosts are in general the most efficient and convenient for the production of recombinant proteins and therefore preferred for the expression of Taq polymerase.

In the particular case of Taq polymerase, evidence indicates that considerable deletion at the N-terminus of the protein may occur under both recombinant and native conditions, and that the activity of the protein is still retained. It appears that the native proteins isolated may be the result of proteolytic degradation, and not translation of a truncated gene. The mutein produced from the truncated gene of plasmid pFC85 is, however, fully active in assays for DNA polymerase, as is that produced from DNA encoding the full-length sequence. Since it is clear that certain N-terminal shortened forms are active, the gene constructs used for expression of the polymerase may also include the corresponding shortened forms of the coding sequence.

Control Sequences and Corresponding Hosts

Procaryotes most frequently are represented by various strains of *E. coli*. However, other microbial strains may also be used, such as bacilli, for example, *Bacillus subtilis*, various species of *Pseudomonas*, or other bacterial strains. In such procaryotic systems, plasmid vectors that contain replication sites and control sequences derived from a species compatible with the host are used. For example, E. coli is typically transformed using derivatives of pBR322, a plasmid derived from an E. coli species by. Bolivar, et al., Gene (1977) 2:95. pBR322 contains genes for ampicillin and tetracycline resistance, and thus provides additional markers that can be either retained or destroyed in constructing the desired vector. Commonly used procaryotic control sequences, which are defined herein to include promoters for transcription initiation, optionally with an operator, along with ribosome binding site sequences, include such commonly used promoters as the β-lactamase (penicillinase) and lactose (lac) promoter systems (Chang, et al., Nature (1977) 198:1056), the tryptophan (trp) promoter system (Goeddel, et al., Nucleic Acids Res. (1980) 8:4057) and the lambda-derived $P_L$ promoter (Shimatake, et al., Nature (1981) 292:128) and N-gene ribosome binding site, which has been made useful as a portable control cassette (as set forth in U.S. Pat. No. 4,711,845, filed Dec. 24, 1984), which comprises a first DNA sequence that is the $P_L$ promoter operably linked to a second DNA sequence corresponding to $N_{RBS}$ upstream of a third DNA sequence having at least one restriction site that permits cleavage within six bp 3' of the $N_{RBS}$ sequence. Also useful is the phosphatase A (phoA) system described by Chang, et al. in European Patent Publication No. 196,864 published Oct. 8, 1986, assigned to the same assignee and incorporated herein by reference. However, any available promoter system compatible with procaryotes can be used.

In addition to bacteria, eucaryotic microbes, such as yeast, may also be used as hosts. Laboratory strains of Saccharomyces cerevisiae, Baker's yeast, are most used, although a number of other strains are commonly available. While vectors employing the 2 micron origin of replication are illustrated (Broach, J. R., Meth. Enz. (1983) 101:307), other plasmid vectors suitable for yeast expression are known (see, for example, Stinchcomb, et al., Nature (1979) 282:39, Tschempe, et al., Gene (1980) 10:157 and Clarke, L., et al., Meth. Enz. (1983) 101:300). Control sequences for yeast vectors include promoters for the synthesis of glycolytic enzymes (Hess, et al., J. Adv. Enzyme Reg. (1968) 7:149; Holland, et al., Biotechnology (1978) 17:4900).

Additional promoters known in the art include the promoter for 3-phosphoglycerate kinase (Hitzeman, et al., J. Biol. Chem. (1980) 255.2073), and those for other glycolytic enzymes, such as glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters that have the additional advantage of transcription controlled by growth conditions are the promoter regions for alcohol dehydrogenase 2, isocytochrome C, acid phosphatase, degradative enzymes associated with nitrogen metabolism, and enzymes responsible for maltose and galactose ultilization (Holland, supra).

It is also believed that terminator sequences are desirable at the 3' end of the coding sequences. Such terminators are found in the 3' untranslated region following the coding sequences in yeast-derived genes. Many of the vectors illustrated contain control sequences derived from the enolase gene containing plasmid peno46 (Holland, M. J., et al., J. Biol. Chem. (1981) 256:1385) or the LEU2 gene obtained from YEp13 (Broach, J., et al., Gene (1978) 8:121); however, any vector containing a yeast-compatible promoter, origin of replication, and other control sequences is suitable.

It is also, of course, possible to express genes encoding polypeptides in eucaryotic host cell cultures derived from multicellular organisms. See, for example, Tissue Culture, Academic Press, Cruz and Patterson, editors (1973). Useful host cell lines include murine myelomas N51, VERO and HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) (Fiers, et al., Nature (1978) 273:113), or other viral promoters such as those derived from polyoma, Adenovirus 2, bovine papiloma virus, or avian sarcoma viruses, or immunoglobulin promoters and heat shock promoters. A system for expressing DNA in mammalian systems using the BPV as a vector is disclosed in U.S. Pat. No. 4,419,446. A modification of this system is described in U.S. Pat. No. 4,601,978. General aspects of mammalian cell host system transformations have been described by Axel, U.S. Pat. No. 4,399,216. It now appears, also, that "enhancer" regions are important in optimizing expression; these are, generally, sequences found upstream of the promoter region. Origins of replication may be obtained, if needed, from viral sources. However, integration into the chromosome is a common mechanism for DNA replication in eucaryotes.

Plant cells are also now available as hosts, and control sequences compatible with plant cells such as the nopaline synthase promoter and polyadenylation signal sequences (Depicker, A., et al., J. Mol. Appl. Gen. (1982) 1:561) are available.

Recently, in addition, expression systems employing insect cells utilizing the control systems provided by baculovirus vectors have been described (Miller, D. W., et al., in Genetic Engineering (1986) Setlow, J. K. et al., eds., Plenum Publishing, Vol. 8, pp. 277–297). These systems are also successful in producing Taq polymerase.

Transformations

Depending on the host cell used, transformation is done using standard techniques appropriate to such cells. The calcium treatment employing calcium chloride, as described by Cohen, S. N., Proc. Natl. Acad. Sci. (USA) (1972) 69:2110 is used for procaryotes or other cells that contain substantial cell wall barriers. Infection with Agrobacterium tumefaciens (Shaw, C. H., et al., Gene (1983) 23:315) is used for certain plant cells. For mammalian cells without such cell walls, the calcium phosphate precipitation method of Graham and van der Eb, Virology (1978) 52:546 is preferred. Transformations into yeast are carried out according to the method of Van Solingen, P., et al., J. Bact. (1977) 130:946 and Hsiao, C. L., et al., Proc. Natl. Acad. Sci. (USA) (1979) 76:3829.

Construction of a λgt11 Expression Library

The strategy for isolating DNA encoding desired proteins such as the Taq polymerase encoding DNA, using the bacteriophage vector lambda gt11, is as follows. A library can be constructed of EcoRI-flanked AluI fragments, generated by complete digestion of Thermus aquaticus DNA, inserted at the EcoRI site in the lambda gt11 phage (Young and Davis, *Proc. Natl. Acad. Sci USA* (1983) 80:1194–1198). Because the unique EcoRI site in this bacteriophage is located in the carboxyl-terminus of the β-galactosidase gene, inserted DNA (in the appropriate frame and orientation) is expressed as protein fused with β-galactosidase under the control of the lactose operon prompter/operator.

Genomic expression libraries are then screened using the antibody plaque hybridization procedure. A modification of this procedure, referred to as "epitope selection," uses antiserum against the fusion protein sequence encoded by the phage, to confirm the identification of hybridized plaques. Thus, this library of recombinant phages could be screened with antibodies that recognize the 86,000–90,000 dalton Taq polymerase in order to identify phage that carry DNA segments encoding the antigenic determinants of this protein.

Approximately $2 \times 10^5$ recombinant phage are screened using total rabbit Taq polymerase antiserum. In this primary. screen, positive signals are detected and one or more of these plaques are purified from candidate plaques which failed to react with preimmune serum and reacted with immune serum and analyzed in some detail. To examine the fusion proteins produced by the recombinant phage, lysogens of the phage in the host Y1089 are produced. Upon induction of the lysogens and gel electrophoresis of the resulting proteins, each lysogen may be observed to produce a new protein, not found in the other lysogens, or duplicate sequences may result. Phage containing positive signals are picked., in this case, one positive plaque was picked for further identification and replated at lower densities to purify recombinants and the purified clones were analyzed by size class via digestion with EcoRI restriction enzyme. Probes can then be made of the isolated DNA insert sequences and labeled appropriately and these probes can be used in conventional colony or plaque hybridization assays described in Maniatis et al., *Molecular Cloning: A Laboratory Manual* (1982), the disclosure of which is incorporated herein by reference.

The labeled probe was used to probe a second genomic library constructed in a Charon 35 bacteriophage (Wilhelmine, A. M. et al., *Gene* (1983) 26:171–179). This library was made from Sau3A partial digestions of genomic *Thermus aquaticus* DNA and size fractionated fragments (15–20 kb) were cloned into the BamHI site of the Charon 35 phage. The probe was used to isolate phage containing DNA encoding the Taq polymerase. One of the resulting phage, designated CH35:Taq#4-2, was found to contain the entire gene sequence. Partial sequences encoding portions of the gene were also isolated.

Vector Construction

Construction of suitable vectors containing the desired coding and control sequences employs standard ligation and restriction techniques that are well understood in the art. Isolated plasmids, DNA sequences, or synthesized oligonucleotides are cleaved, tailored, and religated in the form desired.

Site-specific DNA cleavage is performed by treating with the suitable restriction enzyme (or enzymes) under conditions that are generally understood in the art, and the particulars of which are specified by the manufacturer of these commercially available restriction enzymes. See, e.g., New England Biolabs, Product Catalog. In general, about 1 μg of plasmid or DNA sequence is cleaved by one unit of enzyme in about 20 μl of buffer solution; in the examples herein, typically an excess of restriction enzyme is used to ensure complete digestion of the DNA substrate. Incubation times of about one hour to two hours at about 37° C. are workable, although variations can be tolerated. After each incubation, protein is removed by extraction with phenol/chloroform, and may be followed by o ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* (1980) 65:499–560.

Restriction-cleaved fragments may be blunt-ended by treating with the large fragment of *E. coli* DNA polymerase I (Klenow) in the presence of the four deoxynucleotide triphosphates (dNTPs) using incubation times of about 15 to 25 minutes at 20 to 25° C. in 50 mM Tris pH 7.6, 50 mM NaCl, 10 mM MgCl$_2$, 10 mM DTT and 50–100 μM dNTPs. The Klenow fragment fills in at 5' sticky ends, but chews back protruding 3' single strands, even though the four dNTPs are present. If desired, selective repair can be performed by supplying only one of the, or selected, dNTPs within the limitations dictated by the nature of the sticky ends. After treatment with Klenow, the mixture is extracted with phenol/chloroform and ethanol precipitated. Treatment under appropriate conditions with S1 nuclease results in hydrolysis of any single-stranded portion.

Synthetic oligonucleotides may be prepared using the triester method of Matteucci, et al., (*J. Am. Chem. Soc.* (1981) 103:3185–3191) or using automated synthesis methods. Kinasing of single strands prior to annealing or for labeling is achieved using an excess, e.g., approximately 10 units of polynucleotide kinase to 1 nM substrate in the presence of 50 mM Tris, pH 7.6, 10 mM MgCl$_2$, 5 mM dithiothreitol, 1–2 mM ATP. If kinasing is for labeling of probe, the ATP will contain high specific activity γ-$^{32}$P.

Ligations are performed in 15–30 μl volumes under the following standard conditions and temperatures: 20 mM Tris-Cl pH 7.5, 10 mM MgCl$_2$, 10 mM DTT, 33 μg/ml BSA, 10 mM-50 mM NaCl, and either 40 μM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 μg/ml total DNA concentrations (5–100 nM total end concentration). Intermolecular blunt end ligations (usually employing a 10–30 fold molar excess of linkers) are performed at 1 μM total ends concentration.

In vector construction employing "vector fragments", the vector fragment is commonly treated with bacterial alkaline phosphatase (BAP) in order to remove the 5' phosphate and prevent religation of the vector. BAP digestions are conducted at pH 8 in approximately 150 mM Tris, in the presence of Na$^+$ and Mg$^{+2}$ using about 1 unit of BAP per mg of vector at 60° C. for about one hour. In order to recover the nucleic acid fragments, the preparation is extracted with phenol/chloroform and ethanol precipitated. Alternatively, religation can be prevented in vectors that have been double digested by additional restriction enzyme digestion of the unwanted fragments.

Modification of DNA Sequences

For portions of vectors derived from cDNA or genomic DNA that require sequence modifications, site-specific primer-directed mutagenesis is used. This technique is now standard in the art, and is conducted using a primer synthetic oligonucleotide complementary to a single-stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells that harbor the phage.

Theoretically, 50% of the new plaques will contain the phage having, as a single strand, the mutated form; 50% will have the original sequence. The plaques are transferred to nitrocellulose filters and the "lifts" hybridized with kinased synthetic primer at a temperature that permits hybridization of an exact match, but at which the mismatches with the original strand are sufficient to prevent hydbrodization. Plaques that hybridize with the probe are then picked and cultured, and the DNA is recovered.

Verification of Construction

In the constructions set forth below, correct ligations for plasmid construction are confirmed by first transforming E. coli strain MM294, or other suitable host, with the ligation mixture. Successful transformants are selected by ampicillin, tetracycline or other antibiotic resistance or using other markers, depending on the mode of plasmid construction, as is understood in the ar. Plasmids from the transformants are then prepared according to the method of Clewell, D. B., et al., *Proc. Natl. Acad. Sci. (USA)* (1969) 62:1159, optionally following chloramphenicol amplication (Clewell, D. B., *J. Bacteriol.* (1972). 110:667) 110:667). The isolated DNA is analyzed by restriction and/or sequenced by the dideoxy method of Sanger, F., et al., *Proc. Natl. Acad. Sci. (USA)* (1977) 74:5463 as further described by Messing, et al., *Nucleic Acids Res.* (1981) 9:309, or by the method of Maxam, et al., *Methods in Enzymology* (1980)65:499.

Host Exemplified

Host strains used in cloning and expression herein are as follows:

For cloning and sequencing, and for expression of constructions under control of most bacterial promoters, E. coli strain MM294 obtained from E. coli Genetic Stock Center GCSC #6135, was used as the host. For expression under control of the $P_LN_{RBS}$ promoter, E. coli strain K12 MC1000 lambda lysogen, $N_7N_{53}cI857$ $SusP_{80}$, ATCC 39531 may be used. Used herein is E. coli DG116, which was deposited with ATCC (ATCC 53606) on Apr. 7, 1987.

For M13 phage recombinants, E. coli strains susceptible to phage infection, such as E. coli K12 strain DG98, are employed. The DG98 strain has been deposited with ATCC July 13, 1984 and has accession number 39768.

Mammalian expression can be accomplished in COS-7 COS-A2, CV-1, and murine cells, and insect cell based expression in *Spodoptera frugipeida*).

Stabilization of Enzyme Activity

For long-term stability, the enzyme herein must be stored in a buffer that contains one or more non-ionic polymeric detergents. Such detergents are generally those that have a molecular weight in the range of approximately 100 to 250,000, preferably about 4,000 to 200,000 daltons and stabilize the enzyme at a pH of from about 3.5 to about 9.5, preferably from about 4 to 8.5. Examples of such detergents include those specified on pages 295-298 of McCutcheon's *Emulsifiers & Detergents*, North American edition (1983), published by the McCutcheon Division of MC Publishing Co., 175 Rock Road, Glen Rock, N.J. (USA), the entire disclosure of which is incorporated herein by reference. Preferably, the detergents are selected from the group comprising ethoxylated fatty alcohol ethers and lauryl ethers, ethoxylated alkyl phenols, octylphenoxy polyethoxy ethanol compounds, modified oxyethylated and/or oxypropylated straight-chain alcohols, polyethylene glycol monooleate compounds, polysorbate compounds, and phenolic fatty. alcohol ethers. More particularly preferred are Tween 20, from ICI Americas Inc., Wilmington, Del., which is a polyoxyethylated (20) sorbitan monolaurate, and Iconol ™ NP-40, from BASF Wyandotte Corp. Parsippany, N.J., which is an ethoxylated alkyl Phenol (nonyl).

The thermostable enzyme of this invention may be used for any purpose in which such enzyme is necessary or desirable. In a particularly preferred embodiment, the enzyme herein is employed in the amplification protocol set forth below.

Amplification Protocol

The amplification protocol using the enzyme of the present invention may be the process for amplifying existing nucleic acid sequences that is disclosed and claimed in copending U.S. Pat. No. 4,683,202 filed Oct. 25, 1985, the disclosure of which is incorporated herein by reference. Preferably, however, the enzyme herein is used in the amplification process disclosed and claimed in copending U.S. patent application Ser. No. 899,513 filed Aug. 22, 1986, wherein Cetus Corporation is the assignee, as in the present invention, entitled "Process for Amplifying, Detecting, and/or Cloning Nucleic Acid Sequences Using A Thermostable Enzyme". The disclosure of said latter application is herein incorporated by reference.

More specifically, the amplification method of the latter application involves amplifying at least one specific nucleic acid sequence contained in a nucleic acid or a mixture of nucleic acids, wherein if the nucleic acid is double-stranded, it consists of two separated complementary strands of equal or unequal length, which process comprises:

(a) contacting each nucleic acid strand with four different nucleotide triphosphates and one oligonucleotide primer for each different specific sequence being amplified, wherein each primer is selected to be substantially complementary. to different strands of each specific sequence, such that the extension product synthesized from one primer, when it is separated from its complement, can serve as a template for synthesis of the extension product of the other primer, said contacting being at a temperature which promotes hybridization of each primer to its complementary nucleic acid strand;

(b) contacting each nucleic acid strand, at the same time as or after step (a), with a DNA polymerase from

*Thermus aquaticus* which enables combination of the nucleotide triphosphates to form primer extension products complementary to each strand of each nucleic acid;

(c) maintaining the mixture from step (b) at an effective temperature for an effective time to promote the activity of the enzyme, and to synthesize, for each different sequence being amplified, an extension product of each primer which is complementary to each nucleic acid strand template, but not so high as to separate each extension product from its complementary strand template;

(d) heating the mixture from step (c) for an effective time and at an effective temperature to separate the primer extension products from the templates on which they were synthesized to produce single-stranded molecules, but not so high as to denature irreversibly the enzyme;

(e) cooling the mixture from step (d) for an effective time and to an effective temperature to promote hybridization of each primer to each of the single-stranded molecules produced in step (d); and (f) maintaining the mixture from step (e) at an effective temperature for an effective time to promote the activity of the enzyme and to synthesize, for each different sequence being amplified, an extension product of each primer which is complementary to each nucleic acid strand template produced in step (d), but not so high as to separate each extension product from its complementary strand template wherein the effective time and temperatures in steps (e) and (f) may coincide (steps (e) and (f) are carried out simultaneously), or may be separate.

Steps (d)–(f) may be repeated until the desired level of sequence amplification is obtained.

The amplification method is useful not only for producing large amounts of an existing completely specified nucleic acid sequence, but also for producing nucleic acid sequences which are known to exist but are not completely specified. In either case an initial copy of the sequence to be amplified must be available, although it need not be pure or a discrete molecule.

In general, the amplification process involves a chain reaction for producing, in exponential quantities relative to the number of reaction steps involved, at least one specific nucleic acid sequence given (a) that the ends of the required sequence are known in sufficient detail that oligonucleotides can be synthesized which will hybridize to them, and (b) that a small amount of the sequence is available to initiate the chain reaction. The product of the chain reaction will be a discrete nucleic acid duplex with termini corresponding to the ends of the specific primers employed.

Any nucleic acid sequence, in purified or nonpurified form, can be utilized as the starting nucleic acid(s), provided it contains or is suspected to contain the specific nucleic acid sequence desired. Thus, the process may employ, for example, DNA or RNA, including messenger RNA, which DNA or RNA may be single-stranded or double-stranded. In addition, a DNA-RNA hybrid which contains one strand of each may be utilized. A mixture of any of these nucleic acids may also be employed, or the nucleic acids produced from a previous amplification reaction herein using the same or different primers may be so utilized. The specific nucleic acid sequence to be amplified may be only a fraction of a larger molecule or can be present initially as a discrete molecule, so that the specific sequence constitutes the entire nucleic acid.

It is not necessary that the sequence to be amplified be present initially in a pure form; it may be a minor fraction of a complex mixture, such as a portion of the $\beta$-globin gene contained in whole human DNA (as exemplified in Saiki et al., *Science*, 230, 1530–1534 (1985)) or a portion of a nucleic acid sequence due to a particular microorganism which organism might constitute only a very minor fraction of a particular biological sample. The starting nucleic acid sequence may contain more than one desired specific nucleic acid sequence which may be the same or different. Therefore, the amplification process is useful not only for producing large amounts of one specific nucleic acid sequence, but also for amplifying simultaneously more than one different specific nucleic acid sequence located on the same or different nucleic acid molecules.

The nucleic acid(s) may be obtained from any source, for example, from plasmids such as pBR322, from cloned DNA or RNA, or from natural DNA or RNA from any source, including bacteria, yeast, viruses, organelles, and higher organisms such as plants or animals. DNA or RNA may be extracted from blood, tissue material such as chorionic villi, or amniotic cells by a variety of techniques such as that described by Maniatis et al., supra, p. 280–281.

If probes are used which are specific to a sequence being amplified and thereafter detected, the cells may be directly used without extraction of the nucleic acid if they are suspended in hypotonic buffer and heated to about 90–100° C., until cell lysis and dispersion of intracellular components occur, generally 1 to 15 minutes. After the heating step the amplification reagents may be added directly to the lysed cells.

Any specific nucleic acid sequence can be produced by the amplification process. It is only necessary that a sufficient number of bases at both ends of the sequence be known in sufficient detail so that two oligonucleotide primers can be prepared which will hybridize to different strands of the desired sequence and at relative positions along the sequence such that an extension product synthesized from one primer, when it is separated from its template (complement), can serve as a template for extension of the other primer into a nucleic acid sequence of defined length. The greater the knowledge about the bases at both ends of the sequence, the greater can be the specificity of the primers for the target nucleic acid sequence, and thus the greater the efficiency of the process.

It will be understood that the word "primer" as used hereinafter may refer to more than one primer, particularly in the case where there is some ambiguity in the information regarding the terminal sequence(s) of the fragment to be amplified. For instance, in the case where a nucleic acid sequence is inferred from protein sequence information, a collection of primers containing sequences representing all possible codon variations based on degeneracy of the genetic code will be used for each strand. One primer from this collection will be homologous with the end of the desired sequence to be amplified.

The oligonucleotide primers may be prepared using any suitable method, such as, for example, the phosphotriester and phosphodiester methods described above, or automated embodiments thereof. In one such automated embodiment, diethylphosphoramidites are used as starting materials and may be synthesized as described by Beaucage et al., *Tetrahedron Letters* (1981), 22:1859–1862. One method for synthesizing oligonucleotides on a modified solid support is described in U.S. Pat. No. 4,458,066. It is also possible to use a primer which has been isolated from a biological source (such as a restriction endonuclease digest).

The specific nucleic acid sequence is produced by using the nucleic acid containing that sequence as a template. The first step involves contacting each nucleic acid strand with four different nucleotide triphosphates and one oligonucleotide primer for each different nucleic acid sequence being amplified or detected. If the nucleic acids to be amplified or detected are DNA, then the nucleotide triphosphates are dATP, dCTP, dGTP and TTP.

The nucleic acid strands are used as a template for the synthesis of additional nucleic acid strands. This synthesis can be performed using any suitable method. Generally it occurs in a buffered aqueous solution, preferably at a pH of 7–9, most preferably about 8. Preferably, a molar excess (for cloned nucleic acid, usually about 1000:1 primer:template, and for genomic nucleic acid, usually about $10^6$:1 primer:template) of the two oligonucleotide primers is added to the buffer containing the separated template strands. It is understood, however, that the amount of complementary strand may not be known if the process herein is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

Preferably the concentration of nucleotide triphosphates is 150–200 μM each in the buffer for amplification and $MgCl_2$ is present in the buffer in an amount of 1.5–2 mM to increase the efficiency and specificity of the reaction.

The resulting solution is then treated according to whether the nucleic acids being amplified or detected are double or single-stranded. If the nucleic acids are single-stranded, then no denaturation step need by employed, and the reaction mixture is held at a temperature which promotes hybridization of the primer to its complementary target (template) sequence. Such temperature is generally from about 35° C. to 65° C. or more, preferably about 37–60° C. for an effective time, generally one-half to five minutes, preferably one-three minutes. Preferably, 45–58° C. is used for Taq polymerase and >15-mer primers to increase the specificity of primer hybridization. Shorter primers need lower temperatures.

The complement to the original single-stranded nucleic acid may be synthesized by adding one or two oligonucleotide primers thereto. If an appropriate single primer is added, a primer extension product is synthesized in the presence of the primer, the DNA polymerase from *Thermus aquaticus* and the nucleotide triphosphates. The product will be partially complementary to the single-stranded nucleic acid and will hybridize with the nucleic acid strand to form a duplex of strands of unequal length which may then be separated into single strands as described above to produce two single separated complementary strands. Alternatively, two appropriate primers may be added to the single-stranded nucleic acid and the reaction carried out.

If the nucleic acid contains two strands, it is necessary to separate the strands of the nucleic acid before it can be used as the template. This strand separation can be accomplished by any suitable denaturing method including physical, chemical or enzymatic means. One preferred physical method of separating the strands of the nucleic acid involves heating the nucleic acid until it is completely (>99%) denatured. Typical heat denaturation involves temperatures ranging from about 90° to 105° C. for times generally ranging from about 0.5 to 5 minutes. Preferably the effective denaturing temperature is 90–100° C. for 0.5 to 3 minutes. Strand separation may also be induced by an enzyme from the class of enzymes known as helicases or the enzyme RecA, which has helicase activity and in the presence of riboATP is known to denature DNA. The reaction conditions suitable for separating the strands of nucleic acids with helicases are describe by Kuhn Hoffmann-Berling, *CSH-Quantitative Biology*, 43:63 (1978), and techniques for using RecA are reviewed in C. Radding, *Ann. Rev. Genetics*, 16:405–37 (1982). The denaturation produces two separated complementary strands of equal or unequal length.

If the double-stranded nucleic acid is denatured by heat, the reaction mixture is allowed to cool to a temperature which promotes hybridization of each primer present to its complementary target (template) sequence. This temperature is usually from about 35° C. to 65° C. or more, depending on reagents, preferably 37–60° C., maintained for an effective time, generally 0.5 to 5 minutes, and preferably 1–3 minutes. In practical terms, the temperature is simply lowered from about 95° C. to as low as 37° C., preferably to about 45–58° C. for Taq polymerase, and hybridization occurs at a temperature within this range.

Whether the nucleic acid is single- or double-stranded, the DNA polymerase from *Thermus aquaticus* may be added at the denaturation step or when the temperature is being reduced to or is in the range for promoting hybridization. The reaction mixture is then heated to a temperature at which the activity of the enzyme is promoted or optimized, i.e., a temperature sufficient to increase the activity of the enzyme in facilitating synthesis of the primer extension products from the hybridized primer and template. The temperature must actually be sufficient to synthesize an extension product of each primer which is complementary to each nucleic acid template, but must not be so high as to denature each extension product from its complementary template (i.e., the temperature is generally less than about 80° C.–90° C.).

Depending mainly on the types of enzyme and nucleic acid(s) employed, the typical temperature effective for this synthesis reaction generally ranges from about 40° to 80° C., preferably 50–75° C. The temperature more preferably ranges from about 65–75° C. when a DNA polymerase from *Thermus aquaticus* is employed. The period of time required for this synthesis may range from about 0.5 to 40 minutes or more, depending mainly on the temperature, the length of the nucleic acid, the enzyme and the complexity of the nucleic acid mixture, preferably one to three minutes. If the nucleic acid is longer, a longer time period is generally required. The presence of dimethylsulfoxide (DMSO) is not necessary or recommended because DMSO was found to inhibit Taq polymerase enzyme activity.

The newly synthesized strand and its complementary nucleic acid strand form a double-stranded molecule which is used in the succeeding steps of the process. In the next step, the strands of the double-stranded molecule are separated by heat denaturation at a temperature effective to denature the molecule, but not so high that the thermostable enzyme is completely and irreversibly denatured or inactivated. Depending mainly on the type of enzyme and the length of nucleic acid, this temperature generally ranges from about 90° to 105° C., more preferably 90–100° C., and the time for denaturation typically ranges from 0.5 to four minutes, depending mainly on the temperature and nucleic acid length.

After this time, the temperature is decreased to a level which promotes hybridization of the primer to its complementary single-stranded molecule (template) produced from the previous step. Such temperature is described above.

After this hybridization step, or in lieu of (or concurrently with) the hybridization step, the temperature is adjusted to a temperature that is effective to promote the activity of the thermostable enzyme to enable synthesis of a primer extension product using as template the newly synthesized strand from the previous step. The temperature again must not be so high as to separate (denature) the extension product from its template, as previously described (usually from 40° to 80° C. for 0.5 to 40 minutes, preferably 50° to 70° C. for one-three minutes). Hybridization may occur during this step, so that the previous step of cooling after denaturation is not required. In such a case, using simultaneous steps, the preferred temperature range is 50–70° C.

The heating and cooling steps of strand separation, hybridization, and extension product synthesis can be repeated as often as needed to produce the desired quantity of the specific nucleic acid sequence, depending on the ultimate use. The only limitation is the amount of the primers, thermostable enzyme and nucleotide triphosphates present. Preferably, the steps are repeated at least twice. For use in detection, the number of cycles will depend, e.g., on the nature of the sample. For example, fewer cycles will be required if the sample being amplified is pure. If the sample is a complex mixture of nucleic acids, more cycles will be required to amplify the signal sufficiently for its detection. For general amplification and detection, preferably the process is repeated at least 20 times.

When labeled sequence-specific probes are employed as described below, preferably the steps are repeated at least five times. When human genomic DNA is employed with such probes, the process is repeated preferably 15–30 times to amplify the sequence sufficiently that a clearly detectable signal is produced, i.e., so that background noise does not interfere with detection.

As will be described in further detail below, the amount of the specific nucleic acid sequence produced will accumulate in an exponential fashion.

No additional nucleotides, primers, or thermostable enzyme need be added after the initial addition, provided that the enzyme has not become denatured or inactivated irreversibly, in which case it is necessary to replenish the enzyme after each denaturing step. Addition of such materials at each step, however, will not adversely affect the reaction.

When it is desired to produce more than one specific nucleic acid sequence from the first nucleic acid or mixture of nucleic acids, the appropriate number of different oligonucleotide primers are utilized. For example, if two different specific nucleic acid sequences are to be produced, four primers are utilized. Two of the primers are specific for one of the specific nucleic acid sequences and the other two primers are specific for the second specific nucleic acid sequence. In this manner, each of the two different specific sequences can be produced exponentially by the present process.

After the appropriate length of time has passed to produce the desired amount of the specific nucleic acid sequence, the reaction may be halted by inactivating the enzyme in any known manner (e.g., by adding EDTA, phenol, SDS or $CHCl_3$) or by separating the components of the reaction.

The amplification process may be conducted continuously. In one embodiment of an automated process, the reaction mixture may be temperature cycled such that the temperature is programmed to be controlled at a certain level for a certain time.

One such instrument for this purpose is the automated machine for handling the amplification reaction of this invention described in copending U.S. Ser. No. 833,368 filed Feb. 25, 1986 entitled "Apparatus And Method For Performing Automated Amplification of Nucleic Acid Sequences And Assays Using Heating And Cooling Steps," the disclosure of which is incorporated herein by reference. Briefly, this instrument utilizes a liquid handling system under computer control to make liquid transfers of enzyme stored at a controlled temperature in a first receptacle into a second receptacle whose temperature is controlled by the computer to conform to a certain incubation profile. The second receptacle stores the nucleic acid sequence(s) to be amplified plus the nucleotide triphosphates and primers. The computer includes a user interface through which a user can enter process parameters that control the characteristics of the various steps in the amplification sequence such as the times and temperatures of incubation, the amount of enzyme to transfer, etc.

A preferred machine that may be employed utilizes temperature cycling without a liquid handling system because the enzyme need not be transferred at every cycle. Such a machine is described more completely in copending U.S. application Ser. No. 899,061, filed Aug. 22, 1986, entitled "Apparatus and Method for Performing Automated Amplification of Nucleic Acid Sequences and Assays Using Heating and Cooling Steps," the disclosure of which is incorporated herein by reference. Briefly, this instrument consists of the following systems:

1. A heat-conducting container for holding a given number of tubes, preferably 500 $\mu$l tubes, which contain the reaction mixture of nucleotide triphosphates, primers, nucleic acid sequences, and enzyme.

2. A means to heat, cool, and maintain the heat-conducting container above and below room temperature, which means has an input for receiving a control signal for controlling which of the temperatures at or to which the container is heated, cooled or maintained. (These may be Peltier heat pumps available from Materials Electronics Products Corporation in Trenton, N.J. or a water heat exchanger.)

3. A computer means (e.g., a microprocessor controller), coupled to the input of said means, to generate the signals that control automatically the amplification sequence, the temperature levels, and the temperature ramping and timing.

The amplification protocol is demonstrated diagrammatically below, where double-stranded DNA containing the desired sequence [S] comprised of complementary strands [S+] and [S−] is utilized as the nucleic acid. During the first and each subsequent reaction cycle, extension of each oligonucleotide primer on the original template will produce one new ssDNA molecule product of indefinite length that terminates with only one of the primers. These products, hereafter referred to as "long products," will accumulate in a linear fashion; that is, the amount present after any number of cycles will be proportional to the number of cycles.

The long products thus produced will act as templates for one or the other of the oligonucleotide primers during subsequent cycles and will produce mole- The specific sequence to be amplified, [S], can be depicted diagrammatically as:

[S+]  5′ AAAAAAAAAAXXXXXXXXXXCCCCCCCCCC 3′
[S−]  3′ TTTTTTTTTTYYYYYYYYYYGGGGGGGGGG 5′

The appropriate oligonucleotide primers would be:

Primer 1: 3′GGGGGGGGGG 5′

Primer 2: 5′AAAAAAAAAA 3′ so that if DNA containing [S]

```
. . . zzzzzzzzzzzzzzzzAAAAAAAAAAXXXXXXXXXXCCCCCCCCCCzzzzzzzzzzzzzzzz . . .
. . . zzzzzzzzzzzzzzzzTTTTTTTTTTYYYYYYYYYYGGGGGGGGGGzzzzzzzzzzzzzzzz . . .
``` cules of the desired sequence [S+] or [S−]. These molecules will also function as templates for one or the other of the oligonucleotide primers, producing further [S+] and [S−], and thus a chain reaction can be sustained that will result in the accumulation of [S] at an exponential rate relative to the number of cycles.

By products formed by oligonucleotide hybridizais separated into single strands and its single strands are hybridized to Primers 1 and 2, the following extension reactions can be catalyzed by a thermostable polymerase in the presence of the four nucleotide triphosphates:

```
                    3′              5′
        extends ←——GGGGGGGGGG  Primer 1

. . . zzzzzzzzzzzzzzzzAAAAAAAAAAXXXXXXXXXXCCCCCCCCCCzzzzzzzzzzzzzzzz . . .
original template strand+ original template strand−
. . . zzzzzzzzzzzzzzzzTTTTTTTTTTYYYYYYYYYYGGGGGGGGGGzzzzzzzzzzzzzzzz . . .

Primer 2  AAAAAAAAAA ——→extends
                  5′              3′
```

On denaturation of the two duplexes formed, the products are:

```
3′                                                                    5′
. . . zzzzzzzzzzzzzzzzTTTTTTTTTTYYYYYYYYYYGGGGGGGGGG
newly synthesized long product 1

5′                                                                    3′
. . . zzzzzzzzzzzzzzzzAAAAAAAAAAXXXXXXXXXXCCCCCCCCCCzzzzzzzzzzzzzzzz . . .
original template strand+

3′                                                                    5′
. . . zzzzzzzzzzzzzzzzTTTTTTTTTTYYYYYYYYYYGGGGGGGGGGzzzzzzzzzzzzzzzz . . .
original template strand−

5′                                                                    3′
    AAAAAAAAAAXXXXXXXXXXCCCCCCCCCCzzzzzzzzzzzzzzzz . . .
newly synthesized ling product 2
``` tions other than those intended are not sel acatalytic (except in rare instancesl and thus accumulate at a linear rate.

If these four strands are allowed to rehybrimize with Primers 1 and 2 in the next cycle, the thermostable polymerase will catalyze the following reactions:

```
Primer 2  5′ AAAAAAAAAA ——→extends to here

3′. . . zzzzzzzzzzzzzzzzTTTTTTTTTTYYYYYYYYYYGGGGGGGGGG 5′
newly sunthesized long product 1 extends ←——GGGGGGGGGG 5′  Primer 1

5′. . . zzzzzzzzzzzzzzzzAAAAAAAAAAXXXXXXXXXXCCCCCCCCCCzzzzzzzzzzzzzzzz . . . 3′
original template strand+

Primer 2  5′ AAAAAAAAAA ——→extends
```

```
3'... zzzzzzzzzzzzzzzzzzAAAAAAAAAAXXXXXXXXXXCCCCCCCCCCzzzzzzzzzzzzzzzz ... 5'
original template strand⁻ extends to here ⬅——GGGGGGGGGG 5' Primer 1

5' AAAAAAAAAAXXXXXXXXXXCCCCCCCCCCzzzzzzzzzzzzzzzz ... 3'
newly synthesized long product 2
```

If the strands of the above four duplexes are separated, the following strands are found:

```
5' AAAAAAAAAAXXXXXXXXXXCCCCCCCCCC 3'
newly synthesized [S⁺]

3'... zzzzzzzzzzzzzzzzzzTTTTTTTTTTYYYYYYYYYYGGGGGGGGGG 5'
first cycle synthesized long product 1

3'... zzzzzzzzzzzzzzzzzzTTTTTTTTTTYYYYYYYYYYGGGGGGGGGG 5'
newly synthesized long product 1

5'... zzzzzzzzzzzzzzzzzzAAAAAAAAAAXXXXXXXXXXCCCCCCCCCCzzzzzzzzz ... 3'
original template strand⁺

5' AAAAAAAAAAXXXXXXXXXXCCCCCCCCCCzzzzzzzzzzzzzzzz ... 3'
newly synthesized long product 2

3'... zzzzzzzzzzzzzzTTTTTTTTTTYYYYYYYYYYGGGGGGGGGGzzzzzzzzzzzzzzzz ... 5'
original template strand⁻

3' TTTTTTTTTTYYYYYYYYYYGGGGGGGGGG 5'
newly synthesized [S⁻]

5' AAAAAAAAAAXXXXXXXXXXCCCCCCCCCCzzzzzzzzzzzzzzzz ... 3'
first cycle synthesized long product 2
```

It is seen that each strand which terminates with the oligonucleotide sequence of one primer and the complementary sequence of the other is the specific nucleic acid sequence [S] that is desired to be produced.

The amount of original nucleic acid remains constant in the entire process, because it is not replicated. The amount of the long products increases linearly because they are produced only from the original nucleic acid. The amount of the specific sequence increases exponentially. Thus, the specific sequence will become the predominant species This is illustrated in the following table, which indicates the relative amounts of the species theoretically present after n cycles, assuming 100% efficiency at each cycle:

| Cycle Number | Number of Double Strands After 0 to n Cycles | | |
|---|---|---|---|
| | Template | Long Products | Specific Sequence [S] |
| 0 | 1 | — | — |
| 1 | 1 | 1 | 0 |
| 2 | 1 | 2 | 1 |
| 3 | 1 | 3 | 4 |
| 5 | 1 | 5 | 26 |
| 10 | 1 | 10 | 1013 |
| 15 | 1 | 15 | 32,752 |
| 20 | 1 | 20 | 1,048,555 |
| n | 1 | n | $(2^n-n-1)$ |

When a single-stranded nucleic acid is utilized as the template, only one long product is formed per cycle.

A sequence within a given sequence can be amplified after a given number of amplifications to obtain greater specificity of the reaction by adding after at least one cycle of amplification a set of primers that are complementary to internal sequences (that are not on o the ends) of the sequence to be amplified. Such primers may be added at any stage and will provide a shorter amplified fragment. Alternatively, a longer fragment can be prepared by using primers with non-complementary ends but having some overlap with the primers previously utilized in the amplification.

The amplification method may be utilized to clone a particular nucleic acid sequence for insertion into a suitable expression vector. The vector may be used to transform an appropriate host organism to produce the gene product of the sequence by standard methods of recombinant DNA technology. Such cloning may involve direct ligation into a vector using blunt-end ligation, or use of restriction enzymes to cleave at sites contained within the primers.

In addition, the amplification process can be used for in vitro mutagenesis. The oligodeoxyribonucleotide primers need not be exactly complementary to the DNA sequence that is being amplified. It is only necessary that they be able to hybridize to the sequence sufficiently well to be extended by the thermostable enzyme. The product of an amplification reaction wherein the primers employed are not exactly complementary to the original template will contain the sequence of the primer rather than the template, thereby introducing an in vitro mutation. In further cycles this mutation will be amplified with an undiminished efficiency because no further mispaired priming is required. The mutant thus produced may be inserted into an appropriate vector by standard molecular biological techniques and might confer mutant properties on this vector such as the potential for production of an altered protein.

The process of making an altered DNA sequence as described above could be repeated on the altered DNA using different primers to induce further sequence changes. In this way, a series of mutated sequences could gradually be produced wherein each new addition to the series could differ from the last in a minor way, but from the original DNA source sequence in an increasingly major way. In this manner, changes could be made ultimately which were not feasible in a single step due to the inability of a very seriously mismatched primer to function.

In addition, the primer can contain as part of its sequence a non-complementary sequence, provided that a sufficient amount of the primer contains a sequence that is complementary to the strand to be amplified. For example, a nucleotide sequence that is not complementary to the template sequence (such as, e.g., a promoter, linker, coding sequence, etc.) may be attached at the 5' end of one or both of the primers, and thereby appended to the product of the amplification process. After the extension primer is added, sufficient cycles are run to achieve the desired amount of new template containing the non-complementary nucleotide insert. This allows production of large quantities of the combined fragments in a relatively short period of time (e.g., two hours or less) using a simple technique.

The amplification method may also be used to enable detection and/or characterization of specific nucleic acid sequences associated with infectious diseases, genetic disorders or cellular disorders such as cancer, e.g., oncogenes. Amplification is useful when the amount of nucleic acid available for analysis is very small, as, for example, in the prenatal diagnosis of sickle cell anemia using DNA obtained from fetal cells. Amplification is particularly useful if such an analysis is to be done on a small sample using nonradioactive detection techniques which may be inherently insensitive, or where radioactive techniques are being employed, but where rapid detection is desirable.

For the purposes of this discussion, genetic diseases may include specific deletions and/or mutations in genomic DNA from any organism, such as, e.g., sickle cell anemia, cystic fibrosis, α-thalassemia, β-thalassemia, and the like. Sickle cell anemia can be readily detected via oligomer restriction analysis as described by EP Patent Publication 164,054 published December 11, 1985, or via a RFLP-like analysis following amplification of the appropriate DNA sequence by the amplification method. α-Thalassemia can be detected by the absence of a sequence, and β-thalassemia can be detected by the presence of a polymorphic restriction site closely linked to a mutation that causes the disease.

All of these genetic diseases may be detected by amplifying the appropriate sequence and analyzing it by Southern blots without using radioactive probes. In such a process, for example, a small sample of DNA from, e.g., amniotic fluid containing a very low level of the desired sequence is amplified, cut with a restriction enzyme, and analyzed via a Southern blotting technique. The use of nonradioactive probes is facilitated by the high level of the amplified signal.

In another embodiment, a small sample of DNA may be amplified to a convenient level and then a further cycle of extension reactions performed wherein nucleotide derivatives which are readily detectable (such as $^{32}$P-labeled or biotin-labeled nucleotide triphosphates) are incorporated directly into the final DNA product, which may be analyzed by restriction and electrophoretic separation or any other appropriate method.

In a further embodiment, the nucleic acid may be exposed to a particular restriction endonuclease prior to amplification. Since a sequence which has been cut cannot be amplified, the appearance of an amplified fragment, despite prior restriction of the DNA sample, implies the absence of a site for the endonuclease within the amplified sequence. The presence or absence of an amplified sequence can be detected by an appropriate method.

A practical application of the amplification technique, that is, in facilitating the detection of sickle cell anemia via the oligomer restriction technique [described in EP 164,054, supra, and by Saiki et al., *Bio/Technology*, Vol 3, pp. 1008-1012 (1985)] is described in detail in the Saiki et al. *Science* article cited above. In that *Science* article, a specific amplification protocol is exemplified using a β-globin gene segment.

The amplification method herein may also be used to detect directly single-nucleotide variations in nucleic acid sequence (such as genomic DNA) using sequence-specific oligonucleotides, as described more fully in now abandoned U.S. Ser. No. 839,331 filed Mar. 13, 1986 and in copending U.S. Ser. No. 899,344 filed Aug. 22, 1986, entitled "Process for Detecting Specific Nucleotide Variations and Genetic Polymorphisms Present in Nucleic Acids," which is a continuation-in-part of U.S. Serial No. 839,331, the disclosures of both of which are incorporated herein by reference.

Briefly, in this process, the amplified sample is spotted directly on a series of membranes, and each membrane is hybridized with a different labeled sequence-specific oligonucleotide probe. After hybridization the sample is washed and the label is detected. This technique is especially useful in detecting DNA polymorphisms.

Various infectious diseases can be diagnosed by the presence in clinical samples of specific DNA sequences characteristic of the causative microorganism. These include bacteria, such as Salmonella, Chlamydia, Neisseria; viruses, such as the hepatitis viruses, and Parasites, such as the Plasmodium responsible for malaria. U.S. Patent Reexamination Certificate B1 4,358,535 issued to Falkow et al. on May 13, 1986 describes the use of specific DNA hybridization probes for the diagnosis of infectious diseases. A relatively small number of pathogenic organisms may be present in a clinical sample from an infected patient and the DNA extracted from these may constitute only a very. small fraction of the total DNA in the sample. Specific amplification of suspected pathogen-specific sequences prior to immobilization and detection by hybridization of the DNA samples could greatly improve the sensitivity and specificity of traditional procedures.

Routine clinical use of DNA probes for the diagnosis of infectious diseases would be simplified considerably if nonradioactively labeled probes could be employed as described in EP 63,879 to Ward. In this procedure biotin-containing DNA probes are detected by chromogenic enzymes linked to avidin or biotin-specific antibodies. This type of detection is convenient, but relatively insensitive. The combination of specific DNA amplification by the present method and the use of stably labeled probes could provide the convenience and sensitivity required to make the Falkow et al. and Ward procedures useful in a routine clinical setting.

A specific use of the amplification technology for detecting or monitoring for the AIDS virus is described in now abandoned copending U.S. application Ser. No. 818,127, filed Jan. 10, 1986, the disclosure of which is incorporated herein by reference and repeated in copending U.S. Ser. No. 935,581, filed Nov. 26, 1986, a continuation-in-part of U.S. Ser. No. 818,127. Briefly, the amplification and detection process is used with primers and probes which are designed to amplify and detect, respectively, nucleic acid sequences that are substantially conserved among the nucleic acids in AIDS viruses and specific to the nucleic acids in AIDS viruses. Thus, the sequence to be detected must be sufficiently complementary to the nucleic acids in AIDS viruses to initiate polymerization preferably at room temperature in the presence of the enzyme and nucleotide triphosphates.

The amplification process can also be utilized to produce sufficient quantities of DNA from a single copy human gene such that detection by a simple non-specific DNA stain such as ethidium bromide can be employed to diagnose DNA directly.

In addition to detecting infectious diseases and pathological abnormalities in the genome of organisms, the amplification process can also be used to detect DNA polymorphisms which may not be associated with any pathological state.

In summary, the amplification process is seen to provide a process for amplifying one or more specific nucleic acid sequences using a chain reaction and a thermostable enzyme, in which reaction primer extension products are produced which can subsequently act as templates for further primer extension reactions. The process is especially useful in detecting nucleic acid sequences which are initially present in only very small amounts.

The following examples are offered by way of illustration only and are by no means intended to limit the scope of the claimed invention. In these examples, all percentages are by weight if for solids and by volume if for liquids, unless otherwise noted, and all temperatures are given in degrees Celsius.

EXAMPLE I

1. Synthesis of the Primers

The following two oligonucleotide primers were prepared by the method described below:

5'-ACACAACTGTGTTCACTAGC-3' (PC03)

5'-CAACTTCATCCACGTTCACC-3' (PC04)

These primers, both 20-mers, anneal to opposite strands of the genomic DNA with their 5' ends separated by a distance of 110 base pairs.

A. Automated Synthesis Procedures: The diethylphosphoramidites, synthesized according to Beaucage and Caruthers (Tetrahedron Letters (1981) 22:1859–1862) were sequentially condensed to a nucleoside derivatized controlled pore glass support using a Biosearch SAM-1. The procedure included detritylation with trichloroacetic acid in dichloromethane, condensation using benzotriazole as activating proton donor, and capping with acetic anhydride and dimethylaminopyridine in tetrahydrofuran and pyridine. Cycle time was approximately 30 minutes. Yields at each step were essentially quantitative and were determined by collection and spectroscopic examination of the dimethoxytrityl alcohol released durng detritylation.

B. Oligodeoxyribonucleotide Deprotection and Purification Procedures: The solid support was removed from the column and exposed to 1 ml concentrated ammonium hydroxide at room temperature for four hours in a closed tube. The support was then removed by filtration and the solution containing the partially protected oligodeoxynucleotide was brought to 55° C. for five hours. Ammonia was removed and the residue was applied to a preparative polyacrylamide gel. Electrophoresis was carried out at 30 volts/cm for 90 minutes after which the band containing the product was identified by UV shadowing of a fluorescent plate. The band was excised and eluted with 1 ml distilled water overnight at 4° C. This solution was applied to an Altech RP18 column and eluted with a 7–13% gradient of acetonitrile in 1% ammonium acetate buffer at pH 6.0. The elution was monitored by UV absorbance at 260 nm and the appropriate fraction collected, quantitated by UV absorbance in a fixed volume and evaporated to dryness at room temperature in a vacuum centrifuge.

C. Characterization of Oligodeoxyribonucleotides: Test aliquots of the purified oligonucleotides were $^{32}P$ labeled with polynucleotide kinase and $\gamma$-$^{32}P$-ATP. The labeled compounds were examined by autoradiography of 14–20% polyacrylamide gels after electrophoresis for 45 minutes at 50 volts/cm. This procedure verifies the molecular weight. Base composition was determined by digestion of the oligodeoxyribonucleotide to nucleosides by use of venom diesterase and bacterial alkaline phosphatase and subsequent separation and quantitation of the derived nucleosides using a reverse phase HPLC column and a 10% acetonitrile, 1% ammonium acetate mobile phase.

II. Isolation of Human Genomic DNA from Cell Line

High molecular weight genomic DNA was isolated from a T cell line, Molt 4, homozygous for normal $\beta$-globin available from the Human Genetic Mutant Cell Depository, Camden, NJ as GM2219C using essentially the method of Maniatis et al., supra, p. 280–281.

III. Purification of a Polymerase From *Thermus aquaticus*

*Thermus aquaticus* strain YT1, available without restriction from the American Type Culture Collection, 12301 Parklawn Drive, Rockville, MD, as ATCC No. 25,104 was grown in flasks in the following medium:

| | |
|---|---|
| Sodium Citrate | 1 mM |
| Potassium Phosphate, pH 7.9 | 5 mM |
| Ammonium Chloride | 10 mM |
| Magnesium Sulfate | 0.2 mM |
| Calcium Chloride | 0.1 mM |
| Sodium Chloride | 1 g/l |
| Yeast Extract | 1 g/l |
| Tryptone | 1 g/l |
| Glucose | 2 g/l |
| Ferrous Sulfate | 0.01 mM |

(The pH was adjusted to 8.0 prior to autoclaving.)

A 10-liter fermentor was inoculated from a seed flask cultured overnight in the above medium at 70° C. A total of 600 ml from the seed flask was used to inoculate 10 liters of the same medium. The pH was controlled at 8.0 with ammonium hydroxide with the dissolved oxygen at 40%, with the temperature at 70° C., and with the stirring rate at 400 rpm. After growth of the cells, they were purified using the protocol (with slight modification) of Kaledin et al., supra, through the first five stages and using a different protocol for the sixth stage. All six steps were conducted at 4° C. The rate of fractionation on columns was 0.5 columns/hour and the volumes of radients during elution were 10 column volumes. An alternative and preferred purification protocol is provided in Example VI below.

Briefly, the above culture of the *T. aquaticus* cells was harvested by centrifugation after nine hours of cultivation, in late log phase, at a cell density of 1.4 g dry weight/l. Twenty grams of cells were resuspended in 80 ml of a buffer consisting of 50 mM Tris.HCl pH 7.5, 0.1 mM EDTA. Cells were lysed and the lysate was centrifuged for two hours at 35,000 rpm in a Beckman TI 45 rotor at 4° C. The supernatant was collected (fraction A) and the protein fraction precipitating between 45 and 75% saturation of ammonium sulfate was collected, dissolved in a buffer consisting of 0.2 M potassium phosphate buffer, pH 6.5, 10 mM 2-mercaptoethanol, and 5% glycerine, and finally dialyzed against the same buffer to yield fraction B.

Fraction B was applied to a 2.2×30-cm column of DEAE-cellulose, equilibrated with the above described buffer. The column was then washed with the same buffer and the fractions containing protein (determined by absorbance at 280 nm) were collected. The combined protein fraction was dialyzed against a second buffer, containing 0.01 M potassium phosphate buffer, pH 7.5, 10 mM 2-mercaptoethanol, and 5% glycerine, to yield fraction C.

Fraction C was applied to a 2.6×21-cm column of hydroxyapatite, equilibrated with a second buffer. The column was then washed and the enzyme was eluted with a linear gradient of 0.01–0.5 M potassium phosphate buffer, pH 7.5, containing 10 mM 2-mercaptoethanol and 5% glycerine. Fractions containing DNA polymerase activity (90–180 mM potassium phosphate) were combined, concentrated four-fold using an Amicon stirred cell and YM10 membrane, and dialyzed against the second buffer to yield fraction D.

Fraction D was applied to a 1.6×28-cm column of DEAE-cellulose, equilibrated with the second buffer. The column was washed and the polymerase was eluted with a linear gradient of 0.01–0.5M potassium phosphate in the second buffer. The fractions were assayed for contaminating endonuclease(s) and exonuclease(s) by electrophoretically detecting the change in molecular weight of phage λ DNA or supercoiled plasmid DNA after incubation with an excess of DNA polymerase (for endonuclease) and after treatment with a restriction enzyme that cleaves the DNA into several fragments (for exonuclease). Only those DNA polymerase fractions (65–95 mM potassium phosphate) having minimal nuclease contamination were pooled. To the pool was added autoclaved gelatin in an amount of 250 $\mu$g/ml, and dialysis was conducted against the second buffer to yield Fraction E.

Fraction E was applied to a phosphocellulose column and eluted with a 100 ml gradient (0.01–0.4 M KCl gradient in 20 mM potassium phosphate buffer pH 7.5). The fractions were assayed for contaminating endo/exonuclease(s) as described above as well as for polymerase activity (by the method of Kaledin et al.) and then pooled. The pooled fractions were dialyzed against the second buffer, then concentrated by dialysis against 50% glycerine and the second buffer.

The molecular weight of the polymerase was determined by SDS PAGE. Marker proteins (Bio-Rad low molecular weight standards) were phosphorylase B (92,500), bovine serum albumin (66,200), ovalbumin (45,000), carbonic anhydrase (31,000), soybean trypsin inhibitor (21,500), and lysozyme (14,400).

Preliminary data suggest that the polymerase has a molecular weight of about 86,000–90,000 daltons, not 62,000–63,000 daltons reported in the literature (e.g., by Kaledin et al.).

The polymerase was incubated in 50 $\mu$l of a mixture containing either 25 mM Tris-HCl pH 6.4 on pH 8.0, 0.1 M KCl, 10 mM MgCl$_2$, 1 mM 2-mercaptoethanol, 10 nmoles each of dGTP, dATP, and TTP, and 0.5 $\mu$Ci ($^3$H) dCTP, 8 $\mu$g "activated" calf thymus DNA, and 0.5–5 units of the polymerase. "Activated" DNA is a native preparation of DNA after partial hydrolysis with DNase I until 5% of the DNA was transferred to the acid-soluble fraction. The reaction was conducted at 70° C. for 30 minutes, and stopped by adding 50 $\mu$l of a saturated aqueous solution of sodium pyrophosphate containing 0.125 M EDTA-Na$_2$. Samples were processed and activity was determined as described by Kaledin et al., supra.

The results showed that at pH 6.4 the polymerase was more than one-half as active as at pH 8.0. In contrast, Kaledin et al. found that at pH about 7.0, the enzyme therein had 8% of the activity at pH 8.3. Therefore, the pH profile for the thermostable enzyme herein is broader than that for the Kaledin et al. enzyme.

Finally, when only one or more nucleotide triphosphates were eliminated from a DNA polymerase assay reaction mixture, very little, if any, activity was observed using the enzyme herein, and the activity was consistent with the expected value, and with an enzyme exhibiting high fidelity. In contrast, the activity observed using the Kaledin et al. (supra) enzyme is not consistent with the expected value, and suggests misincorporation of nucleotide triphosphate(s).

IV. Amplification Reaction

One microgram of the genomic DNA described above was diluted in an initial 100 $\mu$l aqueous reaction volume containing 25 mM Tris.HCl buffer (pH 8.0), 50 mM KCl, 10 mM MgCl$_2$, 5 mM dithiothreitol, 200 $\mu$g/ml gelatin, 1 $\mu$M of primer PC03, 1 $\mu$M of primer PC04, 1.5 mM dATP, 1.5 mM dCTP, 1.5 mM dGTP and 1.5 mM TTP. The sample was heated for 10 minutes at 98° C. to denature the genomic DNA, then cooled to room temperature. Four microliters of the polymerase from *Thermus aquaticus* was added to the reaction mixture and overlaid with a 100 $\mu$l mineral oil cap. The sample was then placed in the aluminum heating block of the liquid handling and heating instrument described in copending U.S. application Ser. No. 833,368 filed Feb. 25, 1986, the disclosure of which is incorporated herein by reference.

The DNA sample underwent 20 cycles of amplification in the machine, repeating the following program cycle:

(1) heating from 37° C. to 98° C. in heating block over a period of 2.5 minutes; and (2) cooling from 98° C. to 37° C. over a period of three minutes to allow the primers and DNA to anneal.

After the last cycle, the sample was incubated for an additional 10 minutes at 55° C. to complete the final extension reaction.

V. Synthesis and Phosphorylation of Oligodeoxyribonucleotide Probes

A labeled DNA probe, designated RS24, of the following sequence was prepared:

```
5'-*CCCACAGGGCAGTAACG-
    GCAGACTTCTCCTCAGGAGTCAG-3'
    (RS24)
``` where * indicates the label. This probe is 40 bases long, spans the fourth through seventeenth codons of the gene, and is complementary to the normal β-globin allele (β^A). The schematic diagram of primers and probes is given below:

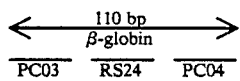

This probe was synthesized according to the procedures described in Section I of Example 1. The probe was labeled by contacting 20 pmole thereof with 4 units of T4 polynucleotide kinase (New England Biolabs) and about 40 pmole γ-$^{32}$P-ATP (New England Nuclear, about 7000 Ci/mmole) in a 40 μl reaction volume containing 70 mM Tris buffer (pH 7.6), 10 mM MgCl$_2$, 1.5 mM sperine, and 10 mM dithiothreitol for 60 minutes at 37° C. The total volume was then adjusted to 100 μl with 25 mM EDTA and the probe purified according to the procedure of Maniatis et al., *Molecular Cloning* (1982), 466–467 over a 1 ml Bio Gel P-4 (BioRad) spin dialysis column equilibrated with Tris-EDTA (TE) buffer (10 mM Tris buffer, 0.1 mM EDTA, pH 8.0). TCA precipitation of the reaction product indicated that for RS24 the specific activity was 4.3 μCi/pmole and the final concentration was 0.118 pmole/μl.

VI. Dot Blot Hybridizations

Four microliters of the amplified sample from Section IV and 5.6 μl of appropriate dilutions of β-globin plasmid DNA calculated to represent amplification efficiencies of 70, 75, 80, 85, 90, 95 and 100% were diluted with 200 μl 0.4 N NaOH, 25 mM EDTA and spotted onto a Genatran 45 (Plasco) nylon filter by first wetting the filter with water, placing it in a Bio-Dot (Bio-Rad, Richmond, CA) apparatus for preparing dot blots which holds the filters in place, applying the samples, and rinsing each well with 0.1 ml of 20×SSPE (3.6 M NaCl, 200 mM NaH$_2$PO$_4$, 20 mM EDTA), as disclosed by Reed and Mann, *Nucleic Acids Research*, 13, 7202–7221 (1985). The filters were then removed, rinsed in 20×SSPE, and baked for 30 minutes at 80° C. in a vacuum oven.

After baking, each filter was then contacted with 16 ml of a hybridization solution consisting of 3×SSPE, 5×Denhardt's solution (1×=0.02% polyvinylpyrrolidone, 0.02% Ficoll, 0.02% bovine serum albumin,, 0.2 mM Tris, 0.2 mM EDTA, pH 8.0), 0.5% SDS and 30% formamide, and incubated for two hours at 42° C. Then 2 pmole of probe RS24 was added to the hybridization solution and the filter was incubated for two minutes at 42° C.

Finally, each hybridized filter was washed twice with 100 ml of 2×SSPE and 0.1% SDS for 10 minutes at room temperature. Then the filters were treated once with 100 ml of 2×SSPE, 0.1% SDS at 60° C. for 10 minutes.

Each filter was then autoradiographed, with the signal readily apparent after two hours.

VII. Discussion of Autoradiogram

The autoradiogram of the dot blots was analyzed after two hors and compared in intensity to standard serial dilution β-globin reconstructions prepared with HaeIII/MaeI-digested pBR:β^A, where β^A is the wild-type allele, as described in Saiki et al., *Science*, supra.

Analysis of the reaction product indicated that the overall amplification efficiency was about 95%, corresponding to a 630,000-fold increase in the β-globin target sequence.

EXAMPLE II

I. Amplification Reaction

Two 1 μg samples of genomic DNA extracted from the Molt 4 cell line as described in Example I were each diluted in a 100 μl reaction volume containing 50 mM KCl, 25 mM Tris.HCl buffer pH 8.0, 10 mM MgCl$_2$, 1 μM of primer PC03, 1 μM of primer PC04, 200 μg/ml gelatin, 10% dimethylsulfoxide (by volume), and 1.5 mM each of dATP, dCTP, dGTP and TTP. After this mixture was heated for 10 minutes at 98° C. to denature the genomic DNA, the samples were cooled to room temperature and 4 μl of the polymerase from *Thermus aquaticus* described in Example I was added to each sample. The samples were overlaid with mineral oil to prevent condensation and evaporative loss. One of the samples was placed in the heating block of the machine described in Example I and subjected to 25 cycles of amplification, repeating the following program cycle:

(1) heating from 37° to 93° C. over a period of 2.5 minutes., (2) cooling from 93° C. to 37° C. over a period of three minutes to allow the primers and DNA to anneal; and (3) maintaining at 37° C. for two minutes.

After the last cycle the sample was incubated for an additional 10 minutes at 60° C. to complete the final extension reaction.

The second sample was placed in the heat-conducting container of the machine, described in more detail in copending U.S. Ser. No. 899,061 filed Aug. 22, 1986. The heat-conducting container is attached to Paltier heat pumps which adjust the temperature upwards or downwards and a microprocessor controller to control automatically the amplification sequence, the temperature levels, the temperature ramping and the timing of the temperature.

The second sample was subjected to 25 cycles of amplification, repeating the following program cycle:

(1) heating from 37° to 95° C. over a period of three minutes;

(2) maintaining at 95° C. for 0.5 minutes to allow denaturation to occur;

(3) cooling from 95° to 37° C. over a period of one minute; and (4) maintaining at 37° C. for one minute.

II. Analysis

Two tests were done for analysis, a dot blot and an agarose gel analysis.

For the dot blot analysis, a labeled DNA probe, designated RS18, of the following sequence was prepared.

5'-*CTCCTGAGGAGAAGTCTGC-3' (RS18)

where * indicates the label. This probe is 19 bases long, spans the fourth through seventeenth codons of the gene, and is complementary. to the normal β-globin allele (β^A). The schematic diagram of primers and probes is given below:

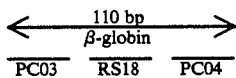

This probe was synthesized according to the procedures described in Section I of Example 1. The probe was labeled by contacting 10 pmole thereof with 4 units of T4 polynucleotide kinase (New England Biolabs) and about 40 pmole γ-$^{32}$P-ATP (New England Nuclear, about 7000 Ci/mmole) in a 40 μl reaction volume containing 70 mM Tris.HCl buffer (pH 7.6 , 10 mM MgCl$_2$, 1.5 mM spermine and 10 mM dithiothreitol for 60 minutes at 37° C. The total volume was then adjusted to 100 μl with 25 mM EDTA and purified according to the procedure of Maniatis et al., supra, p. 466–467 over a 1 ml Bio Gel P-4 (BioRad) spin dialysis column equilibrated with Tris-EDTA (TE) buffer (10 mM Tris.HCl buffer, 0.1 mM EDTA, pH 8.0). TCA precipitation of the reaction product indicated that for RS18 the specific activity was 4.6 μCi/pmole and the final concentration was 0.114 pmole/μl.

Five microliters of the amplified sample from Section I and of a sample amplified as described above except using the Klenow fragment of E. coli DNA Polymerase I instead of the thermostable enzyme were diluted with 195 μl 0.4 N NaOH, 25 mM EDTA and spotted onto two replicate Genatran 45 (Plascol nylon filters by first wetting the filters with water, placing them in a Bio-Dot (Bio-Rad, Richmond, CA) apparatus for preparing dot blots which holds the filters in place, applying the samples, and rinsing each well with 0.4 ml of 20×SSPE (3.6 M NaCl, 200 mM NaH$_2$PO$_4$, 20 mM EDTA), as disclosed by Reed and Mann, supra. The filters were then removed, rinsed in 20×SSPE, and baked for 30 minutes at 80° C. in a vacuum oven.

After baking, each filter was then contacted with 6 ml of a hybridization solution consisting of 5×SSPE, 5'Denhardt's solution (1×=0.02% polyvinylpyrrolidone, 0.02% Ficoll, 0.02% bovine serum albumin, 0.2 mM Tris, 0.2 mM EDTA, pH 8.0) and 0.5% SDS, and incubated for 60 minutes at 55° C. Then 5 ul of probe RS18 was added to the hybridization solution and the filter was incubated for 60 minutes at 55° C.

Finally, each hybridized filter was washed twice with 100 ml of 2×SSPE and 0.1% SDS for 10 minutes at room temperature. Then the filters were treated twice more with 100 ml of 5×SSPE, 0.1% SDS at 60° C. for 1) one minute and 2) three minutes, respectively.

Each filter was then autoradiographed, with the signal readily apparent after 90 minutes.

In the agarose gel analysis, 5 μl each amplification reaction was loaded onto 4% NuSieve/0.5% agarose gel in 1×TBE buffer (0.089 M Tris, 0.089 M boric acid, and 2 mM EDTA) and electrophoresed for 60 minutes at 100V. After staining with ethidium bromide, DNA was visualized by UV fluorescence.

The results show that the machines used in Example I and this example were equally effective in amplifying the DNA, showing discrete high-intensity 110-base pair bands of similar intensity, corresponding to the desired sequence, as well as a few other discrete bands of much lower intensity. In contrast, the amplification method as described in Example I of now abandoned U.S. application Ser. No. 839,331 filed Mar. 13, 1986, supra, which involves reagent transfer after each cycle using the Klenow fragment of E. coli Polymerase I, gave a DNA smear resulting from the non-specific amplification of many unrelated DNA sequences.

It is expected that similar improvements in amplification and detection would be achieved in evaluating HLA-DQ, DR and DP regions.

If in the above experiments the amplification reaction buffer contains 2 mM MgCl$_2$ instead of 10 mM MgCl$_2$ and 150–200 μM of each nucleotide rather than 1.5 mM of each, and if the lower temperature of 37° C. is raised to 45°–58° C. during amplification, better specificity and efficiency of amplification occurs. Also, DMSO was found not necessary or preferred for amplification.

EXAMPLE III

Amplification and Cloning

For amplification of a 119-base pair fragment on the human β-globin gene, a total of 1 microgram each of human genomic DNA isolated from the Molt 4 cell line or from the GM2064 cell line (representing a homozygous deletion of the β- and δ-hemoglobin region and available from the Human Genetic Mutant Cell Depository, Camden, NJ) as described above was amplified in a 100 μl reaction volume containing 50 mM KCl, 25 mM Tris.HCl pH 8, 10 mM MgCl$_2$, 200 μg/ml gelatin, 5 mM 2-mercaptoethanol, 1.5 mM each of dATP, dCTP, TTP, and dGTP, and 1 μM of each of the following primers:

5'-CTTCTGcagCAACTGTGTTCACTAGC-3'
(GH18)

5'-CACaAgCTTCATCCACGTTCACC-3' (GH19)

where lower case letters denote mismatches from wild-type sequence to create restriction enzyme sites. GH18 is a 26-base oligonucleotide complementary to the negative strand and contains an internal PstI site. GH19 is a 29-base oligonucleotide complementary to the plus strand and contains an internal HindIII recognition sequence. These primers were selected by first screening the regions of the gene for homology to the PstI and HindIII restriction sites. The primers were then prepared as described in Example I.

The above reaction mixtures were heated for 10 minutes at 95° C. and then cooled to room temperature. A total of 4 μl of the polymerase described in Example I was added to each reaction mixture, and then each mixture was overlayed with mineral oil. The reaction mixtures were subjected to 30 cycles of amplification with the following program:

2.5 min. ramp, 37° to 98° C.
3 min. ramp, 98° to 37° C.
2 min. soak, 37° C.

After the last cycle, the reaction mixtures were incubated for 20 minutes at 65° C. to complete the final extension. The mineral oil was extracted with chloroform and the mixtures were stored at −20° C.

A total of 10 μl of the amplified product was digested with 0.5 μl M13mp10 cloning vector, which is publicly available from Boehringer-Mannheim, in a 50 μl volume containing 50 mM NaCl, 10 mM Tris.HCl, pH 7.8, 10 mM MgCl$_2$, 20 units PstI and 26 units HindIII for 90 minutes at 37° C. The reaction was stopped by freezing at −20° C. The volume was adjusted to 110 μl with TE buffer and loaded (100 μl) onto a 1 ml BioGel P-4 spin dialysis column. One 0.1 ml fraction was collected and ethanol precipitated.

(At this point it was discovered that there was β-globin amplification product in the GM2064 sample. Subsequent experiments traced the source of contamination to the primers, either GH18 or GH19. Because no other source of primers was available, the experiment was continued with the understanding that some cloned sequences would be derived from the contaminating DNA in the primers.)

The ethano pellet was resuspended in 15 μl water, then adjusted to 20 μl volume containing 50 mM Tris.HCl, pH 7.8, 10 mM $MgCl_2$, 0.5 mM ATP, 10 mM dithiothreitol, and 400 units ligase. This mixture was incubated for three hours at 16° C.

Ten microliters of ligation reaction mixture containing molt 4 DNA was transformed into *E. coli* strain JM103 competent cells, which are publicly available from BRL in Bethesda, MD. The procedure followed for preparing the transformed strain is described in Messing, J. (1981) *Third Cleveland Symposium on Macromolecules:Recombinant DNA*, ed. A. Walton, Elsevier, Amsterdam, 143–163. A total of 651 colorless plaques (and 0 blue plaques) were obtained. Of these, 119 had a (+)strand insert (18%) and 19 had a (−)-strand insert (3%). This is an increase of almost 20-fold over the percentage of β-globin positive plaques among the primer-positive plaques from the amplification technique using klenow fragment of *E. coli* Polymerase I, where the reaction proceeded for two minutes at 25° C., after which the steps of heating to 100° C. for two minutes, cooling, adding klenow fragment, and reacting were repeated nine times. These results confirm the improved specificity of the amplification reaction employing the thermostable enzyme herein.

In a later cloning experiment with GM2064 and the contaminated primers, 43 out of 510 colorless plaques (8%) had the (+)- strand insert. This suggests that approximately one-half of the 119 clones from Molt 4 contain the contaminant sequence.

Ten of the (+)- strand clones from Molt 4 were sequenced. Five were normal wild-type sequence and five had a single C to T mutation in the third position of the second codon of the gene (CAC to CAT). Four of the contaminant clones from GM2064 were sequenced and all four were normal.

Restriction site-modified primers may also be used to amplify and clone and partially sequence the human N-ras oncogene and to clone base pair segments of the HLA DQ-α, DQ-β and DR-β genes using the above technique.

Again, if the concentrations of $MgCl_2$ and nucleotides are reduced to 2 mM and 150–200 μM, respectively, and the minimum cycling temperature is increased from 37° C. to 45°–58° C., the specificity and efficiency of the amplification reaction can be increased.

EXAMPLE IV

Gene Retrieval

A. Identification of a DNA Sequence Probe for the Taq Polymerase Gene.

A specific DNA sequence probe for the Taq pol gene was obtained following immunological screening of a λgt11 expression library. *T. aquaticus* DNA was digested to completion with AluI, ligated with EcoRI 12-mer linkers (CCGGAATTCCGG, New England Biolabs), digested with EcoRI and ligated with dephosphorylated, EcoRI-digested λgt11 DNA (Promega Biotech). The ligated DNA was packaged (Gigapack Plus, Strategene) and transfected into *E. coli* K-12 strain Y1090 (provided by R. Young).

The initial library of $2 \times 10^5$ plaques was screened (Young, R. A., and R. W. Davis (1983) Science, 222:778–782) with a 1:2000 dilution of a rabbit polyclonal antiserum raised to purified Taq polymerase (see Examples I and VI). Candidate plaques were replated at limiting dilution and rescreened until homogeneous (~3 cycles). Phage were purified from candidate plaques which failed to react with preimmune serum and reacted with immune serum.

Candidate phge were used to lysogenize *E. coli* K-12 strain Y1089 (R. Young). Lysogens were screened for the production of an IPTG inducible fusion protein (larger than β-galactosidase) which reacted with the Taq polymerase antiserum. Solid phase, size-fractionated fusion proteins were used to affinity purify epitope-specific antibodies from the total polyclonal antiserum (Goldstein, L. S. B., et al. (1986) J. Cell Biol. 102:2076–2087).

The "fished", epitope-selected antibodies were used, in turn, in a Western analysis to identify which λgt11 phage candidates encoded DNA sequences uniquely specific to Taq polymerase. One λgt11 phage candidate, designated λgt:1, specifically selected antibodies from the total rabbit polyclonal Taq polymerase antiserum which uniquely reacted with both purified Taq polymerase and crude extract fractions containing Taq polymerase. This phage, λgt:1, was used for further study.

The ~115 bp EcoRI-adapted AluI fragment of *Thermus aquaticus* DNA was labeled (Maniatis et al., supra) to generate a Taq polymerase-specific probe. The probe was used in Southern analyses and to screen a *T. aquaticus* DNA random genomic library.

B. Construction and Screening of a Thermus Aquaticus Random Genomic Library.

Lambda phage Charon 35 (Wilhelmine, A. M. et al., supra) was annealed and ligated via its cohesive ends, digested to completion with BamHI, and the annealed arms were purified from the "stuffer" fragments by potassium acetate density gradient ultracentrifugation (Maniatis, et al., supra). *T. aquaticus* DNA was partially digested with Sau3A and the 15–20 kb size fraction purified by sucrose density gradient ultracentrifugation. The random genomic library was - constructed by ligating the target and vector DNA fragments at a 1:1 molar ratio. The DNA was packaged and transfected into *E. coli* K-12 strains LE392 or K802. A library of >20,000 initial phage containing >99% recombinants was amplified on *E. coli* K-12 strain LE392.

The CH35 Taq genomic phage library was screened (Maniatis et al., supra) with the radiolabeled EcoRI insert of λgt11:1. Specifically hybridizing candidate phage plaques were purified and further analyzed. One phage, designated Ch35::4-2, released ≧four *T. aquaticus* DNA fragments upon digestion with HindIII (~8.0, 4.5, 0.8, 0.58 kb)

The four HindIII *T. aquaticus* DNA fragments were ligated with HindIII digested plasmid BSM13+ (3.2 kb, Vector Cloning Systems, San Diego) and individually cloned following transformation of *E. coli* K-12 strain DG98.

The ~8.0 kb HindIII DNA fragment from CH35::4-2 was isolated in plasmid pFC82 (11.2 kb), while the 4.5 kb HindIII DNA fragment from CH35::4-2 was isolated in plasmid pFC83 (7.7 kb).

*E. coli* strain DG98 harboring pFC82 was shown to contain a thermostable, high temperature DNA polymerase activity (Table 1). In addition, these cells synthesize a new ~60 kd molecular weight polypeptide which is immunologically related to Taq DNA polymerase.

The Taq polymerase coding region of the 8.0 kb HindIII DNA fragment was further localized to the lac-promoter proximal 2.8 kb HindIII to Asp718 portion of the 8.0 kb HindIII fragment. This region was subcloned to yield plasmid pFC85 (6.0 kb). Upon induction with IPTG, *E. coli* DG98 cells harboring plasmid pFC85 synthesize up to 100-fold more thermostable, Taq polymerase-related activity (Table 1) than the original parent clone (pFC82/DG98). While cells harboring pFC85 synthesize a significant amount of a thermostable DNA polymerase activity, only a portion of the Taq pol DNA sequence is translated, resulting in the accumulation of a ~60 kd Taq polymerase-related polypeptide.

TABLE 1

Expression of a Thermostable DNA Polymerase Activity in *E. coli*#

| Sample | Units*/ml | |
|---|---|---|
| | −IPTG | +IPTG |
| BSM13/DG98- | — | 0.02 |
| pFC82/DG98 | 2.2 | 2.7 |
| pFC85/DG98 | 11.9 | 643.8 |

Cells were grown to late log phase (+/−IPTG, 10 mM), harvested, sonicated, heated at 75° C. for 20 minutes, centrifuged and the clarified supernatant assayed at 70° C. for DNA polymerase activity.
*1 unit = 1 nM dCTP incorporated in 30 minutes.

EXAMPLE V

Expression of Taq Polymerase

The thermostable gene of the present invention can be expressed in any of a variety of bacterial expression vectors including DG141 (ATCC 39588) and $_pP_LN_{RBS}ATG$, a vector disclosed in commonly owned, U.S. Pat. No. 4,711,845, filed Dec. 24, 1984 (Gelfand et al.), the disclosure of which is incorporated herein by referenee. Both of these host vectors are $_pBR322$ derivatives that have either a sequence containing a tryptophan promoter-operator and ribosome binding site with an operably linked ATG start codon (DG141) or a sequence containing the lambda $P_L$ promoter and gene N ribosome binding site operably linked to an ATG start codon ($_pP_LN_{RBS}ATG$). Either one of these host vectors may be restricted with SacI, and blunt ended with Klenow or S1 nuclease to construct a convenient restriction site for subsequent insertion of the Taq polymerase gene.

The full-length Taq polymerase gene was constructed from the DNA insert fragments subcloned into plasmids pFC83 and pFC85 as follows. Vector BSM13+ (commercially available from Vector Cloning Systems, San Diego, CA) was digested at the unique HindIII site, repaired with Klenow and dNTPs, and ligated with T4 DNA ligase to a BglII octanucleotide linker, 5′-CAGATCTG-3′ (New England Biolabs), and transformed into *E. coli* strain DG98. Plasmids were isolated from Amp$^R$ lacZα+ transformants. One of the clones was digested with BglII and Asp718 restriction enzymes, and the large vector fragment purified by gel electrophoresis.

Next, plasmid pFC83 was digested with BglII and HindIII and the ~750 base pair fragment was isolated. Plasmid pFC85 was digested with HindIII and Asp718 and the ~2.8 kb fragment isolated and joined in a three-piece ligation to the ~750 base pair BglII-HindIII fragment from pFC83 and the BglII-Asp718 vector fragment of BSM13+. This ligation mixture was used to transform E. coli strain DG98 (ATCC 39,768 deposited July 13, 1984) from which Amp$^R$ colonies were selected and an ~6.75 kilobase plasmid (pLSGI) was isolated. Isopropyl-β-D-thiogalactoside (IPTG)-induced DG98 cells harboring pLSGI synthesized Taq DNA polymerase indistinguishable in size from the native enzyme isolated from *T. aquaticus*. Plasmid pLSG1 can then be used to generate a single strand DNA template according to the procedure recommended by Vector Cloning Systems.

Oligonucleotide-directed mutagenesis (see Zoller and Smith, *Nuc. Acids Res.* (1982) 10:6487–6500) can then be used to introduce an SphI restriction site as part of the ATG start codon (upstream of the internal HindIII site in the coding sequence of the Taq polymerase gene). Similarly, a BglII site can be introduced after the carboxyl-terminus of the gene (~0.7 kb upstream from the Asp718 site) to facilitate subcloning of the Taq polymerase gene into an expression vector. After the site-directed mutagenesis is performed, the gene can be isolated from the BSM13+ vector on an ~3.2 kb SphI-BstEII restriction fragment, treated with Klenow fragment and all four dNTPs, and inserted with T4 DNA ligase (blunt-end conditions) into either one of the aforementioned expression vectors, which have been digested with SacI, repaired with Klenow and dNTPs, and treated with calf intestine phosphatase to generate dephosphorylated blunt ends. This ligation mixture is used to transform *E. coli* DG116 and the resulting transformants are screened for production of Taq polymerase. Expression of the enzyme can be confirmed by Western immunoblot analysis and activity analysis.

A greater proportion of the Taq polymerase gene contained within the ~2.8 kb HindIII-Asp718 fragment of plasmid pFC85 can be expressed using, for example, plasmid $_pP_LN_{RBS}ATG$, by operably linking the amino-terminal HindIII restriction site encoding the Taq pol gene to an ATG initiation codon. The product of this fusion upon expression will yield an ~66,000–68,000 dalton truncated polymerase.

This specific construction can be made by digesting plasmid pFC85 with HindIII and treating with Klenow fragment in the presence of dATP, dGTP and dCTP. The resulting fragment is treated further with S1 nuclease to remove any single-stranded extensions, and the resulting DNA digested with Asp718 and treated with Klenow fragment in the presence of all four dNTPs. The recovered fragment can be ligated using T4 DNA ligase to dephosphorylated plasmid $_pP_LN_{RBS}ATG$, which had been digested with SacI and treated with Klenow fragment in the presence of dGTP to construct an ATG blunt end. This ligation mixture can then be used to transformed *E. coli* DGI16 and the transformants screened for production of Taq polymerase. Again, expression can be confirmed by Western immunoblot analysis and activity analysis.

EXAMPLE VI

Purification

The thermostable polymerase may be purified directly from a culture of *Thermus aquaticus* following the example disclosed below or, alternatively, from a bacterial culture containing the recombinantly produced enzyme with only minor modifications necessary in the preparation of the crude extract.

After harvesting by centrifugation, 60 grams of cells were resuspended in 75 ml of a buffer consisting of 50 mM Tris-Cl pH 8, 1 mm EDTA. Cells were lysed in a French Press at 14,000–16,000 PSI after which 4 volumes (300 ml) of additional Tris-EDTA were added. Buffer A ($\beta$-mercaptoethanol to 5 mM and NP-40 and Tween 20 to 0.5% (v/v) each) was added and the solution was sonicated thoroughly while cooling. The resultant homogeneous suspension was diluted further with Buffer A such that the final volume was 7.5–8 times the starting cell weight; this was designated Fraction I.

The polymerase activity in Fraction I and subsequent fractions was determined in a 50 $\mu$l mixture containing 0.025 M TAPS-HCl pH 9.4 (20° C.) 0.002 M $MgcL_2$, 0.05 M KCl, 1 mM 2-mercaptoethanol, 0.2 mM each dGTP, dATP, TTP, 0.1 mM dCTP [$\alpha$-$^{32}$P, 0.05 Ci/mM], 12.5 $\mu$g "activated" salmon sperm DNA and 0.01–0.2 units of the polymerase (diluted in 10 mM Tris-HCl, pH 8, 50 mM KCl, 1 mg/ml autoclaved gelatin, 0.5% NP-40, 0.5% Tween 20, and 1 mM 2-mercaptoethanol). One unit corresponds to 10 nM product in 30 minutes. "Activated" DNA is a native preparation of DNA after partial hydrolysis with DNase I until 5% of the DNA was transferred to the acid-soluble fraction. The reaction was conducted at 74° C. for 10 minutes and then 40 $\mu$l was transferred to 1.0 ml of 50 $\mu$g/ml carrier DNA in 2 mM EDTA at 0° C. An equal volume (1.0 ml) of 20% TCA, 2% sodium pyrophosphate was added. After 15–20 minutes at 0° C. the samples were filtered through Whatman GF/C discs and extensively washed with cold 5% TCA-1% pyrophosphate, followed by cold 95% ethanol, dried and counted.

Fraction I was centrifuged for two hours at 35,000 rpm in a Beckman TI 45 rotor at 2° C. and the collected supernatant was designated Fraction II.

The Taq polymerase activity was precipitated with Polymin P (BRL, Gaithersburg, MD) (10%, w/v, adjusted to pH 7.5 and autoclaved) after the minimum amount of Popymin P necessary to precipitate 90–95% of the activity was determined, which amount was generally found to be between 0.25% and 0.3% final volume.

An appropriate level of Polymin P was added slowly to Fraction II while stirring for 15 minutes at 0° C. This solution was centrifuged at 13,000 rpm for 20 minutes in a Beckman JA 14 rotor at 2° C. The supernatant was assayed for activity and the pellet was resuspended in 1/5 volume of 0.5X Buffer A (diluted 1:2 with $H_2O$). This suspension was recentrifuged and the pellet resuspended in ¼ volume of Buffer A containing 0.4 M KCl. This suspension was homogenized thoroughly and left overnight at 4° C. The homogenate was centrifuged as above and the collected supernatant designated Fraction III.

The protein fraction was collected by "precipitation" at 75% saturation of ammonium sulfate, centrifuged (at 27,000 rpm, SW27 rotor, 30 minutes) and the floating pellicle was resuspended in 50 mM Tris-Cl pH 8, 1 mM EDTA. These steps were repeated and the protein suspension was dialyzed extensively with P-cell buffer (20 mM $KPO_4$ pH 7.5, 0.5 mM EDTA, 5 mM $\beta$-mercaptoethanol, 5% (w/v) glycerol, 0.5% (v/v) NP-40 and Tween 20) containing 80 mM KCl.

The dialysate was transferred to a centrifuge bottle to which was added any recovered protein from sacks rinsed with the P-cell buffer containing 80 mM KCl. Centrifugation was performed at 20,000$\times$g and the time was reduced to 15 minutes. The supernatant was saved and any pellet remaining was washed, extracted with P-cell buffer and 80 mM KCl, and recentrifuged. The supernatants were then combined to form Fraction IV.

Fraction IV was applied to a 2.2$\times$22-cm column of phosphocellulose, equilibrated with the P-cell buffer containing 80 mM KCl. The column was washed (2.5–3 column volumes) with the same buffer and the protein eluted using a linear gradient of 80 to 400 mM KCl in P-cell buffer. Fractions containing DNA polymerase activity ($\sim$0.18–0.20 M KCl) were pooled and concentrated 3–4 fold on an Amicon stirred cell and YM30 membrane. The cell was rinsed with the P-cell buffer without KCl and added to the fraction concentrate (0.15 M KCl adjusted final volume) to form Fraction V.

Fraction V was applied to a 5 ml Heparin Sepharose CL-6B column (Pharmacia) equilibrated with P-cell buffer and 0.15 M KCl. The column was washed with 0.15 M KCl buffer (3–4 column volumes) and the protein eluted with a linear gradient from 0.15 to 0.65 M KCl in P-cell buffer. A 1:10 dilution into diluent without gelatin was made for SDS-PAGE analysis and a subsequent 1:20 dilution into diluent with 1 mg/ml gelatin was made for use in enzyme assays. The activity fractions (eluting at $\sim$0.3 M KCl) were assayed on supercoiled DNA template for specific and non-specific endonucleases/topoisomerase by electrophoretically detecting the change in molecular weight of supercoiled plasmid DNA after incubation with an excess of DNA polymerase. Exonuclease contamination was detected following incubation with small linear DNA fragments. In peak fractions, an 88 kd protein was found to be the major band. The major pool, designated Fraction VI, had the highest polymerase activity with minimal detectable endonuclease activity when this pool was assayed for 30 minutes at 55° C. with $\sim$3–5 polymerase units/600 ng DNA.

Fraction VI was dialyzed against 10 mM $KPO_4$ pH 7.5, 5 mM $\beta$-mercaptoethanol, 5% glycerol, 0.2% NP-40, and 0.2% Tween 20 (HA buffer). The dialyzed sample was applied to a 3 ml column of hydroxyapatite and the enzyme eluted with a linear gradient of 10 to 250 mM $KPO_4$ pH 7.5, HA buffer. DNA polymerase activity began to elute at 75 mM $KPO_4$ with the peak at 100 mM $KPO_4$. Active peak fractions were assayed at 1:100–1:300 dilution. As in the prior chromatography step, a 1:10 dilution in diluent was prepared without gelatin for SDS-PAGE analysis. Fractions with no significant endonuclease or double-strand exonuclease when assayed at 55° C. with 5 polymerase units were pooled and designated Fraction VII.

Fraction VII was dialyzed against a solution of 25 mM sodium acetate pH 5.2, 5% glycerol, 5 mM $\beta$-mercaptoethanol, 0.1 mM EDTA, 0.1% NP-40, and 0.1% Tween 20, adjusted to pH 5 at room temperature. The dialyzed sample was applied to a 2 ml DEAE-Tris-Acryl-M (LKB) column pre-equilibrated and subsequently washed with the same buffer. The fraction containing polymerase activity that did not adhere to the column was pooled and adjusted to 50 mM NaCl in the same buffer to yield Fraction VIII.

Fraction VIII was applied to a 2 ml CM-Tris-Acryl M (LKB) column equilibrated with the same buffer (25 mM sodium acetate, 50 mM NaCl, 5% glycerol, 0.1 mM EDTA, 0.1% NP-40, and 0.1% Tween 20). The column was washed with 4–5 column volumes of the same buffer an the enzyme eluted with a linear gradient from 50 to 400 mM NaCl in sodium acetate buffer. The polymerase activity peak eluted ~0.15-0.20 M NaCl. The polymerase activity was assayed at 1:300 to 1:500 dilution with the first dilution 1:10 into diluent without gelatin for the SDS-PAGE analysis. An assay across the activity peak on supercoiled DNA templates for specific and non-specific endonuclease/topoisomerase using DNA polymerase assay salts (25 mM TAPS-HCl pH 9.4, 2.0 mM MgCl$_2$ and 50 mM KCl) at 74° C. was performed, as well as assays for nucleases on M13 as DNA and pBR322 fragments. Active fractions with no detectable nuclease(s) were pooled and run on a silver stained SDSPAGE mini gel. The results show a single ~88 kd band with a specific activity of ~250,000 units/mg.

This specific activity is more than an order of magnitude higher than that claimed for the previously isolated Taq polymerase and is at least an order of magnitude higher than that for *E. coli* polymerase I.

EXAMPLE VII

The Taq polymerase purified as described above in Example VI was found to be free of any contaminating Taq endonuclease and exonuclease activities. In addition, the Taq polymerase is preferably stored in storage buffer containing from about 0.1 to about 0.5% volume/volume of each non-ionic polymeric detergent employed. More preferably the storage buffer consists of 50% (v/v) glycerol, 100 mM KCl, 20 mM Tris-Cl pH 8.0, 0.1 mM ethylenediaminetetraacetic acid (EDTA), 1 mM dithiothreitol, 0.5% v/v NP-40, 0.5% v/v Tween 20, and 200 μg/ml gelatin, and is preferably stored at −20° C.

The stored Taq polymerase was diluted in a buffer consisting of 25 mM Tris Cl pH 8.0, 20 mM KCl, 1 mM β-mercaptoethanol, 0.5% NP-40, 0.5% Tween-20, and 500 μg/ml gelatin. A reaction buffer was then prepared containing 50 mM KCl, 10 mM Tris-Cl, pH 8.3, 1.5 mM MgCl$_2$, 0.01% (w/v) gelatin, 200 μM each dNTP, 1 μM each of the primers that define a 500 base pair target sequence on a control template from bacteriophage λ, and 2.0-2.5 units Taq polymerase/assay in a final volume of 100 μl. Template was added to the reaction buffer, the sample placed in a 0.5 ml polypropylene tube, and the sample topped with 100 μl of heavy white mineral oil to prevent evaporation.

At least a 10$^5$-fold amplification was achieved when the following conditions were employed, using 1 ng of control template (bacteriophage λ DNA) where the target sequence represented approximately 1% of the starting mass of DNA.

First the template mixture was denatured for one minute, 30 seconds at 94° C. by placing the tube in a heat bath. Then the tube was placed in a heat bath at 37° C. for two minutes. Then the tube was placed in a heat bath at 72° C. for three minutes, and then in the heat bath at 94° C. for one minute. This cycle was repeated for a total of 25 cycles. At the end of the 25th cycle, the heat denaturation step at 94° C. was omitted and replaced by extending the 72° C. incubation step by an additional three minutes. Following termination of the assay, the samples were allowed to cool to room temperature and analyzed as described in previous examples.

The template may be optimally amplified with a different concentration of dNTPs and a different amount of Taq polymerase. Also, the size of the target sequence in the DNA sample will directly impact the minimum time required for proper extension (72° C. incubation step). An optimization of the temperature cycling profile should be performed for each individual template to be amplified, to obtain maximum efficiency.

EXAMPLE VIII

Taq polymerase purified as described above in Example I was formulated for storage as described in the previous example, but without the non-ionic polymeric detergents. When assayed for activity as described in that example, the enzyme storage mixture was found to be inactive. When the NP-40 and Tween 20 were added to the storage buffer, the full enzyme activity was restored, indicating that the presence of the non-ionic detergents is necessary to the stability of the enzyme formulation.

EXAMPLE IX

Several 1 μg samples of human genomic DNA were subjected to 20-35 cycles of amplification as described in Example V, with equivalent units of either Klenow fragment or Taq polymerase, and analyzed by agarose gel electrophoresis and Southern blot. The primers used in these reactions, PC03 and PC04, direct the synthesis of a 110-bp segment of the human beta-globin gene. The Klenow polymerase amplifications exhibited the smear of DNA typically observed with this enzyme, the apparent cause of which is the non-specific annealing and extension of primers to unrelated genomic sequences under what were essentially non-stringent hybridization conditions (1×Klenow salts at 37° C.). Nevertheless, by. Southern blot a specific 110-bp beta-globin target fragment was detected in all lanes. A substantially different electrophoretic pattern was seen in the amplifications done with Taq polymerase where the single major band is the 110-bp target sequence. This remarkable specificity was undoubtedly due to the temperature at which the primers were extended.

Although, like Klenow fragment amplifications, the annealing step was performed at 37° C., the temperature of Taq-catalyzed reactions had to be raised to about 70° C. before the enzyme exhibited significant activity. During this transition from 37° to 70° C., poorly matched primer-template hybrids (which formed at 37° C.) disassociated so that by the time the reaction reached an enzyme-activating temperature, only highly complementary substrate was available for extension. This specificity also results in a greater yield of target sequence than similar amplifications done with Klenow fragment because the non-specific extension products effectively compete for the polymerase, thereby reducing the amount of 110-mer that can be made by the Klenow fragment.

EXAMPLE X

Amplification was carried out of a sample containing 1 μg Molt 4 DNA, 50 mM KCl, 10 mM Tris pH 8.3, 10 mM MgCl$_2$, 0.01% gelatin, 1 μM of each of the following primers (to amplify a 150 bp region):

5'-CATGCCTCTTTGCACCATTC-3'(RS79) and

5'-TGGTAGCTGGATTGTAGCTG-3'(RS80)

1.5 mM of each dNTP, and 5.0 units of Taq polymerase per 100 μl reaction volume. Three additional samples were prepared containing 2.5, 1.3, or 0.6 units of Taq polymerase. The amplification was carried out in the temperature cycling machine described above using the following cycle, for 30 cycles:

from 70° to 98° C. for 1 minute
hold at 98° C. for 1 minute
from 98° C. to 35°, 45° or 55° C. for 1 minute
hold at 35°, 45° or 55° C. for 1 minute from 35°, 45° or 55° C. to 70° C. for 1 minute hold at 70° C. for 30 seconds At 35° C. annealing temperature, the 2.5 units/100 μl Taq enzyme dilution gave the best-signal-to noise ratio by agarose gel electrophoresis over all other Taq polymerase concentrations. At 45° C., the 5 units/100 μl Taq enzyme gave the best signal-to-noise ratio over the other concentrations. At 55° C., the 5 units/100 μl Taq enzyme gave the best signal-to-noise ratio over the other concentrations and over the 45° C. annealing and improved yield. The Taq polymerase has more specificity and better yield at 55° C.

In a separate experiment the Molt 4 DNA was 10-fold serially diluted into the cell line GM2064 DNA, containing no β- or δ-globin sequences, available from the Human Genetic Mutant Cell Depository, Camden, New Jersey, at various concentrations representing varying copies per cell, and amplification was carried out on these samples as described in this example at annealing temperatures of 35° C. and 55° C. At 35° C., the best that can be seen by agarose gel electrophoresis is 1 copy in 50 cells. At 55° C., the best that can be seen is 1/5,000 cells (a 100-fold improvement over the lower temperature), illustrating the importance of increased annealing temperature for Taq polymerase specificity under these conditions.

In a third experiment, DNA from a cell line 368H containing HIV-positive DNA, available from B. Poiesz, State University of New York, Syracuse, NY, was similarly diluted into the DNA from the SCI cell line (deposited with ATCC on Mar. 19, 1985; an EBV-transformed β cell line homozygous for the sickle cell allele and lacking any HIV sequences at various concentrations representing varying copies per cell, and amplification was carried out as described in this Example at annealing temperatures of 35° C. and 55° C., using the primers SK38 and SK39, which amplify a 115 bp region of the HIV sequence:

5'-ATAATCCACCTATCCCAGTAG-GAGAAAT-3'(SK38) and

5'-TTTGGTCCTTGTCTTATGTCCAGAATGC-3'(SK39)

The results by agarose gel electrophoresis showed that only the undiluted 368H sample could be detected with the annealing temperature at 35° C., whereas at least a $10^{-2}$ dilution can be detected with the annealing temperature at 55° C., giving a 100-fold improvement in detection.

The following bacteriophage and bacterial strains were deposited with the Cetus Master Culture Collection, 1400 Fifty-Third Street, Emeryville, Calif., USA (CMCC) and with the American Type Culture Collection, 12301 Parklawn Drive, Rockville, Md., USA (ATCC). These deposits were made under the provisions of the Budapest Treaty on the International Recognition of the Deposit of Microorganisms for purposes of Patent Procedure and the Regulations thereunder (Budapest Treaty). This assures maintenance of a viable culture for 30 years from the date of deposit. The organisms will be made available by ATCC under the terms of the Budapest Treaty, and subject to an agreement between applicants and ATCC that assures unrestricted availability upon issuance of the pertinent U.S. patent. Availability of the deposited strains is not to be construed as a license to practice the invention in contravention of the rights granted under the authority of any government in accordance with its patent laws.

| Deposit Designation | CMCC No. | ATCC No. | Deposit |
| --- | --- | --- | --- |
| CH35:Taq #4-2 | 3125 | ATCC 40336 | 5/28/87 |
| E. coli DG98/ pFC83 | 3128 | ATCC 67422 | 5/28/87 |
| E. coli DG98/ pFC85 | 3127 | ATCC 67421 | 5/28/87 |

The foregoing written specification is considered to be sufficient to enable one skilled in the art to practice the invention. The present invention is not to be limited in scope by the cell lines deposited, since the deposited embodiment is intended as a single illustration of one aspect of the invention and any cell lines that are functionally equivalent are within the scope of this invention. The deposit of materials therein does not constitute an admission that the written description herein contained is inadequate to enable the practice of any aspect of the invention, including the best mode thereof, nor are the deposits to be construed as limiting the scope of the claims to the specific illustrations that they represent. Indeed, various modifications of the invention in addition to those shown and described herein will become apparent to those skilled in the art from the foregoing description and fall within the scope of the appended claims.

What is claimed is:

1. Purified thermostable Thermus aquaticus DNA polymerase that migrates on a denaturing polyacrylamide gel faster than phosphorylase B and more slowly than does bovine serum albumin and has an estimated molecular weight of 86,000–90,000 daltons when compared with a phosphorylase B standard assigned a molecular weight of 92,500 daltons 2. The polymerase of claim 1 that is isolated from *Thermus acquaticus*.

3. The polymerase of claim 1 that is isolated from a recombinant organism transformed with a vector that codes for the expression of *Thermis aquaticus* DNA polymerase.

* * * * *

(12) EX PARTE REEXAMINATION CERTIFICATE (5797th)
United States Patent
Gelfand et al.

(10) Number: US 4,889,818 C1
(45) Certificate Issued: Jul. 3, 2007

(54) PURIFIED THERMOSTABLE ENZYME

(75) Inventors: David H. Gelfand, Oakland, CA (US);
Susanne Stoffel, El Cerrito, CA (US);
Frances C. Lawyer, Oakland, CA
(US); Randall K. Saiki, Richmond, CA
(US)

(73) Assignee: Roche Molecular Systems, Inc.,
Branchburg, NJ (US)

Reexamination Request:
No. 90/006,184, Jan. 10, 2002
No. 90/006,805, Oct. 9, 2003

Reexamination Certificate for:
Patent No.: 4,889,818
Issued: Dec. 26, 1989
Appl. No.: 07/063,509
Filed: Jun. 17, 1987

Related U.S. Application Data

(63) Continuation-in-part of application No. 06/899,241, filed on Aug. 22, 1986, now abandoned.

(51) Int. Cl.
*C12N 9/12* (2006.01)

(52) U.S. Cl. ........................ 435/194; 536/23.2
(58) Field of Classification Search .................. 435/194, 435/252.33; 536/23.2
See application file for complete search history.

(56) References Cited

U.S. PATENT DOCUMENTS

| 4,683,195 A | 7/1987 | Mullis et al. |
| 4,683,202 A | 7/1987 | Mullis |
| 5,079,352 A | 1/1992 | Gelfand et al. |

OTHER PUBLICATIONS

Longely et al. "Characterization of the 5' to 3' exonuclease associated with *Thermus aquaticus* DNA polymerase" Nucleic Acid Res. 1990, vol. 18 (24), 7317–7322.*

Alice Jai–yun Chien, 1976, Purification and Characterization of DNA Polymerase from *Thermus aquaticus*. A thesis submitted to the Division of Graduate Studies of the University of Cincinnati.

Alice Chien et al., 1976, Deoxyribonucleic Acid Polymerase from the Extreme Thermophile *Thermus aquaticus*. J. of Bacteriology, vol. 127(2):1550–1557.

David Bruce Edgar, 1972, DNA Polymerase from an Extreme Thermophile: *Thermus aquaticus*. A dissertation submitted to the Division of Graduate Studies of the University of Cincinnati.

Kaledin et al., 1980, Isolation and Properties of DNA Polymerase from Extreme Thermophilic Bacterium: *Thermus aquaticus* YT1. Biochemistry 45:494–501.

Docket sheet of *Hoffman–La Roche, et al. v. Promega Corporation* (N.D. Cal.).

Plaintiffs' memorandum in support of their motion for partial summary judgment on defendants's affirmative defense and counterclaim respecting the validity of the '818 patent.

Declaration of Jennifer Gordon in support of plaintiffs' motion for partial summary judgment of validity (with Exhibits 1–17).

Defendant's opposition to plaintiffs' motion for partial summary judgment of validity.

(Continued)

*Primary Examiner*—Nashaat T. Nashed

(57) ABSTRACT

A purified thermostable enzyme is obtained that has unique characteristics. Preferably the enzyme is isolated from the *Thermus aquaticus* species and has a molecular weight of about 86,000-90,000 daltons. The thermostable enzyme may be native or recombinant and may be used in a temperature-cycling chain reaction wherein at least one nucleic acid sequence is amplified in quantity from an existing sequence with the aid of selected primers and nucleotide triphosphates. The enzyme is preferably stored in a buffer of non-ionic detergents that lends stability to the enzyme.

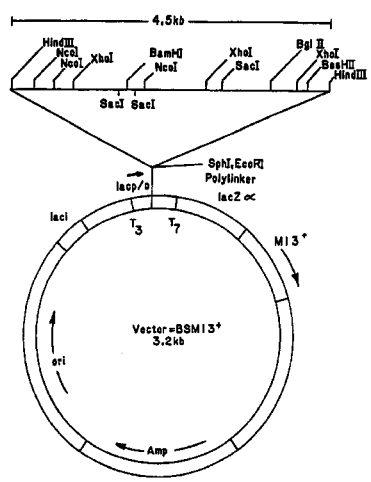

OTHER PUBLICATIONS

Promega's additional statement of facts in opposition to plaintiffs' motion for summary judgment.
Defendant's response to plaintiffs' separate statement of undisputed material facts in support of defendant's opposition to plaintiffs' motion for partial summary judgment of validity and defendant's statement of material undisputed facts.
Affidavit of Dr. Randall L. Dimond in support of defendant's opposition to plaintiff's motion for partial summary judgment of validity (with Exhibits 1–12).
Affidavit of Dr. David B. Edgar in support of defendant's opposition to plaintiffs' motion for partial summary judgment of validity (with Exhibit 1).
Affidavit of Dr. Arthur Kornberg in support of defendant's opposition to plaintiffs' motion for partial summary judgment of validity (with Exhibits 1–2).
Affidavit of Dr. Thomas A. Kunkel in support of defendant's opposition to plaintiffs' motion for partial summary judgment of validity (with Exhibits A–C).
Affidavit of Dr. John J. McDonnell in support of defendant's opposition to plaintiffs' motion for partial summary judgment of validity (with Exhibit 1).
Affidavit of Dr. Dale W. Mosbaugh in support of defendant's opposition to plaintiffs' motion for partial summary judgment of validity (with Exhibits 1–2).
Affidavit of Dr. Peter G. Carroll in support of defendant's opposition to plaintiffs' motion for partial summary judgment of validity (with Exhibits 1–33).
Promega's brief in support of its motion for summary judgment of invalidity of the Taq patent for lack of novelty.
Declaration of Donald A. Cowan in support of Promega's motion for summary judgment of invalidity of the Taq patent for lack of novelty (with Exhibits 1–9).
Declaration of Randall L. Dimond in support of Promega's motion for summary judgment of invalidity of the Taq patent for lack of novelty (with Exhibits 1–10).
Declaration of David B. Edgar in support of Promega's motion for summary judgment of invalidity of the Taq patent for lack of novelty (with Exhibit 1).
Declaration of Arthur Kornberg, M.D., in support of Promega's motion for summary judgment of invalidity of the Taq patent for lack of novelty (no Exhibits).
Declaration of Mark S. Klekamp in support of Promega's motion for summary judgment of invalidity of the Taq patent for lack of novelty (with Exhibits 1–4).
Declaration of Thomas A. Kunkel in support of Promega's motion for summary judgment of invalidity of the Taq patent for lack of novelty (with Exhibits 1–6).
Declaration of Virginia S. Medlen in support of Promega's motion for summary judgment of invalidity of the Taq patent for lack of novelty (with Exhibits 1–36).
Declaration of Dale W. Mosbaugh in support of Promega's motion for summary judgment of invalidity of the Taq patent for lack of novelty (with Exhibits 1–5).
Declaration of Frank J. Ruzicka in support of Promega's motion for summary judgment of invalidity of the Taq patent for lack of novelty (with Exhibits 1–6).
Declaration of Jerilyn Verhoeven in support of Promega's motion for summary judgment of invalidity of the Taq patent for lack of novelty (with Exhibits 1–2).
Plaintiff's opposition to Promega's motion for summary judgment of invalidity of the Taq patent for lack of novelty.
Declaration of Michael J. Chamberlin, Ph.D. (with Exhibits 1–17).
Declaration of Jennifer Gordon in support of plaintiffs' opposition to Promega's motion for summary judgment of invalidity of the Taq patent for lack of novelty (with Exhibits 1–34).
Declaration of Hope Liebke, Esq.
Declaration of Rafael Vicufia (with Exhibits 1–25).
Promega's Reply Brief in support of its motion for summary judgment of invalidity of the Taq patent for lack of novelty.
Declaration of Kamrin T. MacKnight in reply in support of defendant's motion of summary judgment of invalidity of the Taq patent for lack of novelty (with Exhibits 1–12).
Declaration of Thomas J. Burke in support of Promega's motion for summary judgment of invalidity of the Taq patent for lack of novelty (with Exhibit A).
Declaration of Richard John Roberts (with Exhibits 1–2).
Affidavit of Alan Smallwood (with Exhibits 1–2).
Promega's brief in support of its motion for summary judgment of invalidity, filed Oct. 4, 1996.
Declaration of David B. Edgar in support of Promega's motion for summary judgment of invalidity of the Taq patent for lack of novelty.
Declaration of Dr. Diane Rein in support of defendant's motion for summary judgment of invalidity of the '818 patent based on lack of novelty (with Exhibits 1–3).
Plaintiffs' opposition to Promega's motion for summary judgment of invalidity and plaintiffs' cross–motion for partial summary judgment of non–anticipation.
Statement of facts in support of Roche's response to Promega's second motion for summary judgment of invalidity of the '818 patent.
Declaration of Dr. Michael Chamberlin in support of Roche's opposition and cross–motion to Promega's second summary judgment motion of invalidity (with Exhibits 1–16).
Declaration of David H. Gelfand in support of Roche's opposition and cross–motion to Promega's second summary judgment motion of invalidity (with Exhibits A–B).
Declaration of Jennifer Gordon in support of plaintiffs' opposition to Promega's motion for summary judgment of invalidity and plaintiffs' cross–motion for partial summary judgment of non–anticipation (with Exhibits 1–20).
Declaration of Ulrich Hubscher in support of Roche's opposition and cross–motion to Promega's second summary judgment motion of invalidity (with Exhibits 1–23).
Declaration of Walter J. Laird, Ph.D. in support of Roche's opposition and cross–motion to Promega's second summary judgment motion of invalidity (with Exhibits 1–19).
Declaration of Lloyd R. Snyder, Ph.D. in support of Roche's opposition and cross–motion to Promega's second summary judgment motion of invalidity (with Exhibits 1–13).
Declaration of Professor Thomas A. Steitz in support of Roche's opposition and cross–motion to Promega's second summary judgment motion of invalidity (with Exhibits 1–24).
Declaration of Professor Rafael Vicuna in support of Roche's oppositon and cross–motion to Promega's second summary judgment motion of invalidity (with Exhibits 1–33).
Corrected plaintiffs' opposition to Promega's motion for summary judgment of invalidity and plaintiffs' cross–motion for partial summary judgment of non–anticipation filed Nov. 15, 1996.

Corrected declaration of Jennifer Gordon in support of plaintiffs' opposition to Promega's motion for summary judgment of invalidity and plaintiffs' cross–motion for partial summary judgment of non–anticipation filed Nov. 15, 1996 (with Exhibits 1–21).

Promega's reply brief in support of its motion for summary judgment of invalidity of the *Taq* patent for lack of novelty.

Promega's brief in opposition to Roche's cross–motion for partial summary judgment of non–anticipation.

Declaration of Dr. Edward Arnold in support of Promega's motion for summary judgment of invalidity and/or in support of Promega's opposition to Roche's motion and cross–motion for partial summary judgment of non–anticipation (with Exhibits 1–18).

Declaration of Dr. Richard Burgess in support of Promega's motion for summary judgment of invalidity and/or in support of Promega's opposition to Roche's motion and cross–motion for partial summary judgment of non–anticipation (with Exhibits 1–11).

Declaration of Dr. Donald Cowan in support of Promega's motion for summary judgment of invalidity and/or in support of Promega's opposition to Roche's motion and cross–motion for partial summary judgment of non–anticipation (with Exhibits 1–4).

Declaration of Dr. Charles Craik in support of Promega's motion for summary judgment of invalidity and/or in support of Promega's opposition to Roche's motion and cross–motion for partial summary judgment of non–anticipation (with Exhibits 1–4).

Declaration of Dr. Randall Dimond in support of Promega's motion for summary judgment of invalidity and/or in support of Promega's opposition to Roche's motion and cross–motion for partial summary judgment of non–anticipation (with Exhibits 1–19).

Declaration of Dr. Arthur Kornberg in support of Promega's motion for summary judgment of invalidity and/or in support of Promega's opposition to Roche's motion and cross–motion for partial summary judgment of non–anticipation (with Exhibits 1–7).

Declaration of Todd A. Lorenz in support of defendant's opposition to plaintiffs' cross–motion for partial summary judgment of non–anticipation (with Exhibits 1–7).

Declaration of Dr. Ralph R. Meyer in support of Promega's motion for summary judgment of invalidity and/or in support of Promega's opposition to Roche's motion and cross–motion for partial summary judgment of non–anticipation (with Exhibits 1–35).

Declaration of Dale W. Mosbaugh in support of Promega's motion for summary judgment of invalidity and/or in support of Promega's opposition to Roche's motion and cross–motion for partial summary judgment of non–anticipation (with Exhibits 1–30).

Declaration of Dr. Diane Rein in support of Promega's motion for summary judgment of invalidity and/or in support of Promega's opposition to Roche's motion and cross–motion for partial summary judgment of non–anticipation (with Exhibits 1–29).

Defendant's response and objection to plaintiffs' statement of facts in support of Roche's response to Promega's second motion for summary judgment of invalidity of the '818 patent.

Corrected declaration of Dr. Richard Burgess in support of Promega's motion for summary judgment of invalidity and/or in support of Promega's opposition to Roche's motion and cross–motion for partial summary judgment of non–anticipation (with Exhibits 1–11).

Corrected declaration of Dr. Randall Dimond in support of Promega's motion for summary judgment of invalidity and/or in support of Promega's opposition to Roche's motion and cross–motion for partial summary judgment of non–anticipation (with Exhibits 1–23).

Corrected declaration of Todd A. Lorenz in support of defendant's opposition to plaintiffs' cross–motion for partial summary judgment of non–anticipation (with Exhibits 1–7).

Corrected declaration of Dr. Ralph R. Meyer in support of Promega's motion for summary judgment of invalidity and/or in support of Promega's opposition to Roche's motion and cross–motion for partial summary judgment of non–anticipation (with Exhibits 1–37).

Corrected declaration of Dr. Diane Rein in support of Promega's motion for summary judgment of invalidity and/or in support of Promega's opposition to Roche's motion and cross–motion for partial summary judgment of non–anticipation (with Exhibits 1–29).

Promega's motion for discovery under rule 56(f) in response to Roche's submission of new expert declarations containing new information, new opinions, and new conclusions (with Exhibits A–D).

Promega's brief in support of motion to strike portions of declarations in support of Roche's opposition and cross–motion to Promega's motion for summary judgment of invalidity (with Exhibits A–B).

Roche's opposition to Promega's motion to strike and motion for discovery under rule 56(f).

Declaration of Jennifer Gordon in support of Roche's opposition to Promega's moton to strike and motion for discovery under rule 56(f) (with Exhibits A–I).

Plaintiffs' reply in support of cross–motion for partial summary judgment of non–anticipation.

Declaration of Jennifer Gordon for Roche's reply in support of cross–motion for partial summary judgment of non–anticipation (with Exhibits 22–26).

Second declaration of Professor Ulrich Hubscher in support of plaintiffs' reply in their cross–motion for partial summary judgment of non–anticipation (with Exhibits A–U).

Declaration of Randall Saiki in support of Roche's reply for summary judgment of non–anticipation (with Exhibits A–G).

Third declaration of Professor Rafael Vicuna in support of Roche's reply for summary judgment of non–anticipation (with Exhibits A–E).

Promega's reply brief in support of their motion to strike and motion for discovery under rule 56(f).

Roche's memorandum in support of its renewed motion for summary judgment of non–anticipation.

Declaration of Dr. Michael Chamberlin in support of Roche's renewed motion of summary judgment of non–anticipation (with Exhibits A–R).

Declaration of Jennifer Gordon in support of Roche's renewed motion of summary judgment of non–anticipation (with Exhibits 1–32).

Promega's notice of ex parte motion, ex parte motion and memorandum in support of ex parte motion to stay or strike Roche's renewed motion for summary judgment of non–anticipation.

Declaration of John C. Scheller in support of Promega's motion to stay or strike Roche's renewed motion for summary judgment of non–anticipation (with Exhibits A–E).
Letter to Court by Jennifer Gordon regarding Promega's ex parte motion to strike.
Promega's memorandum in opposition to Roche's renewed motion for summary judgment of non–anticipation.
Declaration of Dr. Edward Arnold in support of Promega's opposition to Roche's renewed motion for summary judgment of non–anticipation [with Exhibit A, Exhibit B (with Tabs 1–4)].
Declaration of Dr. Hitomi Asahara in support of Promega's opposition to Roche's renewed motion for summary judgment of non–anticipation (with Exhibits A–B).
Declaration of Gerald Bjorge in support of Promega's opposition to Roche's renewed motion for summary judgment of non–anticipation (with Exhibit A).
Declaration of Dr. Thomas Brock in support of Promega's opposition to Roche's renewed motion for summary judgment of non–anticipation (with Exhibit A).
Declaration of Dr. Richard Burgess in support of Promega's opposition to Roche's renewed motion for summary judgment of non–anticipation [with Exhibit A, Exhibit B (with Tabs 1–5)].
Declaration of Dr. Donald A. Cowan in support of Promega's opposition to Roche's renewed motion for summary judgment of non–anticipation [with Exhibit A, Exhibit B (with Tabs 1–4)].
Declaration of Dr. Charles Craik in support of Promega's opposition to Roche's renewed motion for summary judgment of non–anticipation [with Exhibit A, Exhibit B (with Tabs 1–3)].
Declaration of Dr. Randall Dimond in support of Promega's opposition to Roche's renewed motion for summary judgment of non–anticipation [with Exhibit A, Exhibit B (with Tabs 1–12)].
Declaration of Dr. David Bruce Edgar in support of Promega's opposition to Roche's renewed motion for summary judgment non–anticipation (with Exhibit A).
Second declaration of Dr. David Bruce Edgar in support of Promega's opposition to Roche's renewed motion for summary judgment (no exhibits).
Declaration of Dr. Alex Kaledin in support of Promega's opposition to Roche's renewed motion for summary judgment of non–anticipation (with Exhibits A–B).
Declaration of Dr. Stephen Keller in support of Promega's opposition to Roche's renewed motion for summary judgment of non–anticipation.
Declaration of Dr. Leszek J. Klimczak in support of Promega's opposition to Roche's renewed motion for summary judgment of non–anticipation (with Exhibit A).
Declaration of Dr. Arthur Kornberg in support of Promega's opposition to Roche's renewed motion for summary judgment of non–anticipation [with Exhibit A, Exhibit B (with Tabs 1–7)].
Declaration of Rebecca Kucera in support of Promega's opposition to Roche's renewed motion for summary judgment of non–anticipation [with Exhibit A, Exhibit B (with Tabs 1–2)].
Declaration of Dr. Thomas A. Kunkel in support of Promega's opposition to Roche's renewed motion for summary judgment of non–anticipation [with Exhibit A, Exhibit B (with Tabs 1–5)].
Declaration of Dr. Stuart Linn in support of Promega's opposition to Roche's renewed motion for summary judgment of non–anticipation [with Exhibit A, Exhibit B (with Tabs 1–4)].
Declaration of Dr. Kenneth Marians in support of Promega's opposition to Roche's renewed motion for summary judgment of non–anticipation (with Exhibit A).
Declaration of Ralph Meyer in support of Promega's opposition to Roche's renewed motion for summary judgment of non–anticipation [with Exhibit A, Exhibit B (with Tabs 1–4)].
Declaration of Dr. Dale W. Mosbaugh in support of Promega's opposition to Roche's renewed motion for summary judgment of non–anticipation [with Exhibit A, Exhibit B (with Tabs 1–9)].
Declaration of Dr. Huge Nimmo in support of Promega's opposition to Roche's renewed motion for summary judgment non–anticipation (with Exhibit A).
Declaration of Gayle A. Pellett in support of Promega's opposition to Roche's renewed motion for summary judgment non–anticipation (with Exhibits 1–16).
Declaration of Dr. Diane Rein in support of Promega's opposition to Roche's renewed motion for summary judgment of non–anticipation [with Exhibit A, Exhibit B (with Tabs 1–7)].
Declaration of Dr. Richard J. Roberts in support of Promega's opposition to Roche's renewed motion for summary judgment of non–anticipation [with Exhibit A, Exhibit B (with Tabs 1–5)].
Declaration of Dr. Frank J. Ruzicka in support of Promega's opposition to Roche's renewed motion for summary judgment of non–anticipation [with Exhibit A, Exhibit B (with Tabs 1–3)].
Declaration of Dr. Ronald R. Sederoff in support of Promega's opposition to Roche's renewed motion for summary judgment of non–anticipation (with Exhibits A–B).
Declaration of Jerilyn A. Verhoeven in support of Promega's opposition to Roche's renewed motion for summary judgment of non–anticipation (with Exhibit A).
Declaration of Dr. Ross W. Whetten in support of Promega's opposition to Roche's renewed motion for summary judgment of non–anticipation (with Exhibits A–B).
Promega's notice of motion, motion and memorandum in support of motion to strike Roche's renewed motion for summary judgment of non–anticipation.
Roche's opposition to Promega's motion to strike (with Exhibits 1–2).
Plaintiff's notice of motion, motion and memorandum in support of motion to strike.
Roche's reply brief in support of its renewed motion for summary judgment of non–anticipation.
Declaration of Todd A. Wagner in support of Roche's renewed motion for summary judgment of non–anticipation (with Exhibits 1–12).
Defendant's notice of motion and motion to amend defendant's answer under Rule 15(a) FED.R.CIV.P.
Declaration of Dr. Randall L. Dimond in support of defendant's moton to amend defendant's answer to include the claim of inequitable conduct (with Exhibits 1–15).
Plaintiffs' memorandum in response to defendant's motion for leave to file a third amended answer and counterclaim.
Declaration of Vanessa Wells (with Exhibits A–E).
Defendant's reply in support of defendant's motion for leave to amend answer under rule 15(a).

Affidavit in support of motion to amend (with Exhibits A–B).
Promega's memorandum in support of its motion for summary judgment of unenforceability of the '818 patent based on the applicants' inequitable conduct.
Declaration of Gerald H. Bjorge, Esquire in support of defendant's motion for summary judgment of unenforceability of the '818 patent based on the applicants' inequitable conduct [with Exhibit 1 (with Tabs A–C)].
Declaration of Todd A. Lorenz in support of defendant's motion for summary judgment of unenforceability of the '818 patent based on the applicants' inequitable conduct (with Exhibits 1–28).
Declaration of Dr. Dale W. Mosbaugh in support of defendant's motion for summary judgment of unenforceability of the '818 patent based on the applicants' inequitable conduct [with Exhibit 1 (with Tabs A–C)].
Roche's opposition to Promega's motion for summary judgment of unenforceability of the '818 patent based on alleged inequitable conduct.
Declaration of David H. Gelfand, Ph.D. in support of Roche's opposition to Promega's motion for summary judgment of unenforceability of the '818 patent based on alleged inequitable conduct (with Exhibits 1–23).
Declaration of Jennifer Gordon pursuant to Fed. R. Civ. P.56(f) in support of Roche's opposition to Promega's motion for summary judgment of unenforceability of the '818 patent based on alleged inequitable conduct.
Declaration of Jennifer Gordon in support of Roche's opposition to Promega's motion for summary judgment of unenforceability of the '818 patent based on alleged inequitable conduct (with Exhibits 1–31).
Defendant's reply to plaintiffs' opposition to defendant's motion for summary judgment of unenforceability of the '818 patent based on the applicants' inequitable conduct.
Supplemental declaration of Dr. Dale W. Mosbaugh in support of defendant's motion for summary judgment of unenforceability of the '818 patent based on the applicants' inequitable conduct.
Supplemental declaration of Gerald H. Bjorge, Esquire in support of defendant's motion for summary judgment of unenforceability of the '818 patent based on the applicants' inequitable conduct.
Declaration of Cynthia Soumoff (With Exhibits 1–3).
Plaintiffs' expedited motion pursuant to Civil L.R. 7–9 and 7–10 requesting leave to file a motion for reconsideration of the court's Aug. 9 1996 order granting–in–part defendant's motion for summary judgment of alleged inequitable conduct.
Promega's response in opposition to motion for leave to file motion for reconsideration.
Memorandum in support of defendant's motion under Rule 37, Fed. R. Civ. P., to compel production of Cetus documents withheld by Plaintiff.
Plaintiffs' opposition to defendant's motion pursuant to Fed. R. Civ. P. 37 to compel the production of plaintiff's privileged documents.
Declaration of Robert Drummond, Ph.D. (with Exhibits A–B).
Declaration of David H. Gelfand, Ph.D. (with Exhibits 1–26).
Defendant's reply memorandum motion pursuant to Fed. R. Civ. P. 37 to compel the production of documents withheld by plaintiff on a claim of privilege.
Order denying Promega's motion under Rule 37, Fed. R. Civ. P., to compel production of documents withheld by Plaintiffs on the basis of privilege.
Promega's notice of motion and motion for reconsideration of the magistrate's order denying Promega's motion to compel production of documents withheld by plaintiff on a claim of privilege.
Declaration of Michael E. Husmann (with Exhibits A–D).
Roche's opposition to Promega's motion for reconsideration of Chief Magistrate Judge Langford's order denying Promega's motion pursuant to Fed. R. Civ. P. 37 to compel the production of Roche's privileged documents.
Declaration of Jennifer Gordon in support of Roche's opposition to Promega's motion for reconsideration of Chief Magistrate's Judge Langford order denying Promega's motion pursuant to Fed. R. Civ. P. 37 to compel the production of Roche's privileged documents (with Exhibits 1–8, Tabs within Exhibits 4, 5, 6, 7,8).
Brief in support of Promega's motion for additional discovery.
Roche's response and opposition to Promega's motion for additional discovery.
Declaration of Thomas G. Rowan in support of Roche's response and opposition to Promega's motion for additional discovery (with Exhibits A–B).
Promega's reply brief in support of its motion for additional discovery.
Declaration of J. Donald Best in support of Promega's motion for additional discovery (with Exhibit A–E).
Promega's memorandum in support of its motion to compel production of documents on Roche's withheld document logs.
Declaration of Denise D. Meyers in support of Promega's memorandum in support of its motion to compel production of documents on Roche's withheld document logs (with Exhibits A–B).
Roche's opposition to Promega's motion to compel.
Promega's reply memorandum in support of its motion to compel production of documents on Roche's withheld document logs.
Declaration of Gayle A. Pellett in support of Promega's reply memorandum in support of its motion to compel production of documents on Roche's withheld document logs (with Exhibits 1–13).
Memorandum in support of defendant's motion for summary judgment of invalidity of the '818 patent pursuant to 35 U.S.C.§ 112 ("Best Mode" and "Enablement").
Declaration of Diane E. Ingolia in support of defendant's motion for summary judgment of invalidity of the '818 patent pursuant to 35 U.S.C.§ 112 ("Best Mode" and "Enablement") (with Exhibits 1–15).
Declaration of Stuart M. Linn in support of defendant's motion for summary judgment of invalidity of the '818 patent pursuant to 35 U.S.C.§ 112 ("Best Mode" and "Enablement") (with Exhibits 1–3).
Declaration of Richard John Roberts in support of defendant's motion for summary judgment of invalidity of the '818 patent pursuant to 35 U.S.C.§ 112 ("Best Mode" and "Enablement") (with Exhibits 1–3).
Roche's opposition to Promega's motion for summary judgment of invalidity of the '818 patent pursuant to 35 U.S.C.§ 112 ("Best Mode" and "Enablement").

Declaration of David H. Gelfand, Ph.D. in support of Roche's opposition to Promega's motion for summary judgment of invalidity of the '818 patent pursuant to 35 U.S.C.§ 112 ("Best Mode" and "Enablement") (with Exhibit 1–4).
Declaration of Jennifer Gordon pursuant to Fed. R. Civ. P. 56(f) in support of Roche's opposition to Promega's motion for summary judgment of invalidity of the '818 patent pursuant to 35 U.S.C.§ 112 ("Best Mode" and "Enablement") (with Exhibits A–D).
Declaration of Jennifer Gordon in support of Roche's opposition to Promega's motion for summary judgment of invalidity of the '818 patent under 35 U.S.C.§ 112 ("Best Mode" and "Enablement") (with Exhibit 1–14).
Declaration of Professor Patrick H. O'Farrell in support of Roche's opposition to Promega's motion for summary judgment of invalidity of the '818 patent under 35 U.S.C.§ 112 ("Best Mode" and "Enablement") (with Exhibits 1–4).
Promega's reply brief in support of its motion for summary judgment regarding invalidity of the '818 patent under 35 U.S.C.§ 112 ("Best Mode" and "Enablement").
Supplemental declaration of Dr. Stuart M. Linn in support of defendant's motion for summary judgment of invalidity of the '818 patent under 35 U.S.C.§ 112 ("Best Mode" and "Enablement").
Declaration of Todd Lorenz in support of defendant's reply to plaintiffs' opposition of defendant's motion for summary judgment of invalidity of the '818 patent under 35 U.S.C.§ 112 ("Best Mode" and "Enablement").
Supplemental declaration of Dr. Richard J. Roberts in support of defendant's motion for summary judgment of invalidity of the '818 patent under 35 U.S.C.§ 112 ("Best Mode" and "Enablement").
Memorandum in support of plaintiffs' motion for summary judgment of infringement of claims 1 and 2 of the '818 patent.
Declaration of Hope Liebke, Esq. In support of plaintiffs' motion for summary judgment of infringement of claims 1 and 2 of the '818 patent [with Exhibit s1–15, Exhibit 4 (with Tabs A–O)].
Promega's brief in opposition to Roche's motion for summary judgment of infringement of claims 1 and 2 of the '818 patent and cross–motion for invalidity on the grounds of indefiniteness.
Declaration of Dr. Hitomi Asahara in support of Promega's opposition to Roche's motion for summary judgment of infringement of claims 1 and 2 of the '818 patent and in support for Promega's cross–motion for invalidity on the grounds of indefiniteness.
Declaration of Dr. Randall Dimond in support of Promega's opposition to Roche's motion for summary judgment of infringement of claims 1 and 2 of the '818 patent and in support for Promega's cross–motion for invalidity on the grounds of indefiniteness (with Exhibits 1–3).
Declaration of Dr. Stuart Linn in support of Promega's opposition to Roche's motion for summary judgment of infringement claims 1 and 2 of the '818 patent and in support for Promega's cross–motion for invalidity on the grounds of indefiniteness.
Declaration of Dr. Diane Rein in support of Promega's opposition to Roche's motion for summary judgment of infringement of claims 1 and 2 of the '818 patent and/or in support for Promega's cross–motion for invalidity on the grounds of indefiniteness.

Plaintiffs' reply in support of their motion for summary judgment of infringement of claims 1 & 2 of the '818 patent and opposition to defendant's cross–motion for invalidity on the grounds of indefiniteness.
Declaration of Jennifer Gordon in support of plaintiffs' reply in their motion for summary judgment of infringement of claims 1 and 2 of the '818 patent and opposition to defendant's cross–motion for invalidity on the grounds of indefiniteness (with Exhibits 1–5).
Declaration of Jennifer Gordon pursuant to Fed. R. Civ. P. 56(f).
Declaration of Professor Michael J. Chamberlin in support of plaintiffs' reply in their motion for summary judgment of infringement of claims 1 and 2 of the '818 patent and opposition to defendant's cross–motion for invalidity on the grounds of indefiniteness (with Exhibits A–H).
Promega's reply brief in support of its motion for summary judgment of invalidity on the grounds of indefiniteness.
Declaration of Dr. Dale W. Mosbaugh in support of Promega's motion for summary judgment of invalidity of the '818 patent on the grounds of indefiniteness (with Exhibits 1–5).
Promega's supplemental brief regarding its cross–motion for invalidity of the '818 patent on the grounds of indefiniteness.
Promega's supplemental brief in support of its motion for summary judgment of invalidity of the *Taq* patent on the ground of anticipation.
Declaration of Randall Dimond in support of Promega's supplemental brief regarding its cross–motion for invalidity of the '818 patent on the grounds of anticipation and indefiniteness (with Exhibit 1).
Declaration of Thomas A. Kunkel in support of Promega's supplemental brief regarding its cross–motion for invalidity of the '818 patent on the grounds of anticipation and indefiniteness.
Declaration of Dale W. Mosbaugh in support of Promega's supplemental brief regarding its cross–motion for invalidity of the '818 patent on the grounds of anticipation and indefiniteness (with Exhibits 1–5).
Declaration of Richard J. Roberts in support of Promega's supplemental brief regarding its cross–motion for invalidity of the '818 patent on the grounds of anticipation and indefiniteness.
Plaintiffs' supplemental memorandum in support of plaintiffs' cross–motion for partial summary judgment of non–anticipation.
Declaration of Jennifer Gordon in support of plaintiffs' supplemental memorandum in support of plaintiffs' cross–motion for partial summary judgment of non–anticipation (with Exhibits 27–30).
Plaintiffs' supplemental memorandum opposing Promega's motion for summary judgment of invalidity on the grounds of indefiniteness (with Exhibits 27–30).
Roche's supplemental response to Promega's new arguments on invalidity of the '818 patent on grounds of indefiniteness.
Declaration of Professor Hamilton O. Smith in support of Roche's supplemental response to Promega's new arguments on invalidity of the '818 patent on grounds of indefiniteness (with Exhibits A–K).
Declaration of Jennifer Gordon in support of Roche's supplemental response to Promega's new arguments on invalidity of the '818 patent on grounds of indefiniteness (with Exhibits 1–2).

Declaration of Jennifer Gordon pursuant to Fed. R. Civ. P. 56(f).
Declaration of Professor Sir Aaron Klug, OM PRS in support of Roche's supplemental response to Promega's new arguments on invalidity of the '818 patent on grounds of indefiniteness (with Exhibit A).
Notice of motion and motion to strike Roche's "supplemental response" and for other relief (with Exhibit A).
Roche's opposition to Promega's motion to strike Roche's supplemental response and for other relief.
District court order dated Feb. 26, 1997 (Additional briefing regarding patentability of naturally occurring substances).
Promega's brief in response to the court's order of Feb. 26, 1997.
Declaration of Virginia S. Medlen in support of Promega's brief in response to the court's order of Feb. 26, 1997 (with Exhibits 1–24).
Plaintiffs' brief concerning patentability of claims directed to naturally occurring proteins.
Promega's reply to Roche's brief concerning patentability of claims directed to naturally occurring proteins.
Plaintiffs' reply pursuant to the court's order of Feb. 26, 1997.
Declaration of Jennifer Gordon in support of plaintiffs' reply pursuant to the court's order of Feb. 26, 1997 (with Exhibits 1–3).
District Court order dated Mar. 11, 1998 (additional briefing regarding "thermostable").
Promega's memorandum in support of a finding of indefiniteness (response to Mar. 11, 1998 order).
Plaintiffs' memorandum regarding construction of the term "thermostable", filed pursuant to the court's order dated Mar. 11, 1998.
Declaration of Jennifer Gordon in support of plaintiffs' memorandum regarding construction of the term "thermostable", filed pursuant to the court's order dated Mar. 11, 1998 (with Exhibits 1–5).
Promega's motion to strike declaration of Jennifer Gordon (with Exhibit A).
Roche's opposition to Promega's motion to strike Declaration of Jennifer Gordon.
District Court order dated Jun. 13, 1994 (inter alia, motion to amend answer to include claim of inequitable conduct).
District Court order dated Jul. 3, 1995 (inter alia, $2^{nd}$ round of validity summary judgment motions).
District Court order dated Aug. 9, 1996 (claim construction, inequitable conduct summary judgment motion).
District Court order dated Sep. 5, 1996 (Roche's motion for reconsideration).
District Court order dated Jun. 3, 1997 (construction of "thermostability").
District Court order dated Dec. 31, 1997 (summary judgment motions on invalidity for anticipation and indefiniteness and infringement).
District Court order dated Apr. 29, 1998 (construction of "thermostability").
District Court order dated Dec. 7, 1999 (Inequitable conduct).
District Court order dated Apr. 4, 2000 entering judgment.
Stipulation and order to stay proceedings dated Apr. 12, 2000.
District Court order dated May 8, 2000 regarding administrative closing of files.
Roche's second amended complaint dated Jul. 1995.
Promega's answer to second amended complaint, counter claims and demand for trial by Jury dated Aug. 1, 1995.
Plaintiffs' reply to the counter claims in defendant's answer to plaintiffs second amended complaint.
Brief for plaintiffs—Appellants Hoffman–La Roche Inc. and Roche Molecular Systems, Inc. in CAFC.
Brief for defendant—Appellee Promega Corporation in CAFC.
Reply brief for plaintiffs' appellants, Hoffmann–La Roche Inc. and Roche Molecular Systems, Inc. in CAFC.
Joint appendix for Plaintiffs–Appellants and Defendant–Appellee.
Decision dated Aug. 30, 2001 of opposition division of European Patent Office regarding European Patent No. EP–B–0258017.
Decision dated Nov. 12, 1997 of a Delegate of the Commissioner of Patents (Australia) regarding Patent Application No. 632857.
Declaration under 37 C.F.R. § 1.132 of Henry Erlich from the file history of U.S. Patent. No. 4,683,202.
Transcript of deposition of Alex S. Kaledin, Ph.D. dated Jan. 9, 1996 (with Exhibits).
Transcript of deposition of Jerilyn Verhoeven, dated Jan. 5, 1995.
Patent Opposition Brief filed by Koji Okada in connection with Japanese Patent Application No. 60–207421 (translation) with translations of Exhibits 2–4 and Exhibit 5 (in English).
Patent Opposition Brief filed by Toyobo Co., Ltd. in connection with Japanese Patent Application No. 60–207421 (translation) with translation of Exhibit 2, Experimental Report of Dr. Tobe.
Patent Opposition Brief filed by Yutaka Sato in connection with Japanese Patent Application No. 60–207421 (translation).
Patent Opposition Brief filed by Keiko Nishimura in connection with Japanese Patent Application No. 60–207421 (translation) with translation of Exhibit 3.
Patent Opposition Brief filed by Martin Daum in connection with Japanese Patent Application No. 60–207421 (translation) with translation of Exhibit 2 (Declaration of Dr. Höltke) and Exhibit 6 (in English).
Experimental Report of Drs. Westermann and Sellman filed by Martin Daum in connection with Japanese Patent Application No. 60–207421 (German translation).
Decisions dated Sep. 7, 1993 of the Japanese Patent Office regarding the 5 oppositions of Japanese Patent Application No. 60–207421 (translation).
Translation of claim of Japanese Patent Application No. 60–207421 (now Japanese Patent No. 1,814,713).
Patent Opposition Brief filed by Isabella Mischel in connection with Japanese Patent application No. 2,502,042 (translation) with partial translation of Exhibit 4.
Notice For Reasons for Revocation of Japanese Patent application No. 2,502,042 dated Feb. 25, 1997 (translation).
Translation of claims of Japanese Patent application No. 2,502,042.
Decision dated Jan. 18, 2000 of opposition division of European Patent Office regarding European Patent No. EP–B–0395736.
Grounds of Appeal by Opponent Bioline (UK) Limited against the decision dated Jan. 18, 2000 of the European Patent Office regarding European Patent No. EP–B–0395736.
Rein et al., 1995, *Abstracts of the General Meeting of the American Society for Microbiology* 95:554.
Jan. 28, 2005 Order from *Hoffmann–La Roche Inc.* v. *Promega Corp.*, C–93–1748 (VRW) (N.D. Cal.).

Aug. 20, 2004 Order from *United States of America ex rel. Promega Corporation, et al.* v. *Hoffmann–LaRoche Inc., et al.*, C–03–1447–A (E.D. Va.); Sep. 29, 2004 Order and Memorandum Opinion from United States of America ex rel. Promega Corporation, et al. v. Hoffmann–La Roche Inc., et al., C–03–1447–A (E.D. Va.).

Excerpt from Amended Complaint from *United States of America ex rel. Promega Corporation, et al.* v. *Hoffmann–La Roche Inc., et al.*, C–03–1447–A (E.D. Va.) (pp. 11–26).

Sep. 23, 2004 Class Action Complaint from *Molecular Diagnostics Laboratories* v. *Hoffman–La Roche Inc., et al.*, 1:04 CV 01649 (Dist. Columbia).

English Translation of Jan. 28, 2005 Nullity Brief filed by Promega Corp. in *Promega Corp.* v. *F. Hoffmann–La Roche AG*, German Federal Patent Court and English Translation of Expert Opinion by Prof. Dr. Eggehard Holler in *Promega Corp.* v. *F. Hoffmann–La Roche AG*, German Federal Patent Court.

Oct. 30, 2002 Letter to the Australian Commissioner of Patents re: Amending AU 632857.

Oct. 5, 2004 Outline of Submissions by NEB in *NEB, Inc* v. *F. Hoffmann–La Roche AG*, No. N1305 of 2003 (Federal Court of Australia).

Oct. 5, 2004 Outline of Submissions by Roche in *NEB, Inc.* v. *F. Hoffmann–La Roche AG*, No. N1305 of 2003 (Federal Court of Australia).

Apr. 26, 2005 Supplementary Summary of Argument by NEB in *NEB, Inc.* v. *F. Hoffmann–La Roche AG*, No S345 of 2004 (High Court of Australia).

Jan. 11, 2005 Letter filed on behalf of F. Hoffmann–La Roche AG to the European Patent Office re: Appeal T 0340/00 (EP 0 395 736).

Mar. 31, 2005 Decision of the European Patent office Technical Board of Appeal in No. T340/00–338 (EP 0 395 736).

Excerpt from Jan. 4–5, 1996 deposition of Dale W. Mosbaugh (pp. 175–190).

Excerpts from Dec. 15, 1995 deposition of Donald Arthur Cowan (pp. 45–53, 155–158).

Excerpt from Nov. 27, 1995 deposition of Richard J. Roberts, Ph.D. (pp. 203–207).

In situ activity gels (PR 303432A and PR 303435A).

Excerpt from Aug. 22–24, 1994 deposition transcript of Fen Huang (pp. 246–267).

Excerpt from Fen Huang laboratory notebook (PR 216569–72).

English translation of laboratory notes and records relating to experiments reported in the Declaration of Dr. Höltke filed with the Patent Opposition Brief filed by Martin Daum in connection with Japanese patent application No. 60–207421.

Edgar et al., 1975, "Purification and Characterization of a DNA Polymerase From an Extreme Thermophile, *Thermus Acquaticus*," Abstracts of Annual Meeting of the Annual Meeting of the American Society of Microbiology 75:151 (K26).

Excerpts from Laboratory Notebooks of Susanna Stoffel No. 2297, pp. 133 and 185, and No. 2412, pp. 63–66 and 71–72.

Weber & Osborne, "The Reliability of Molecular Weight Determination by Dodecyl Sulfate–PolyAcrylamide Gel Electrophoresis," J. Biol. Chem. 244:4406–4412 (1969).

Affidavit of Robert Gerard Wakefield in connection with Appeal from decision regarding Australian patent application No. 632857.

Request to Amend Specification dated Jun. 19, 2000, filed in connection with Australian Application No. 632857.

Letter dated May 16, 2000 to Australian Patent Office regarding amendments in Australian Application No. 632857.

Laboratory notebook from Roche Diagnostics GmbH, recording attempts to reproduce the Edgar thesis, plus English translation.

Additional data and analyses related to the Roche Diagnostics GmbH experiments.

Expert Report of Angela Belt, Ph.D.

Composition of Roche Diagnostics GmbH's media for commercial scale culture of *Thermus Aquaticus* for production of Taq I restriction endonuclease.

Poonian et al., 1971, "Covalent Attachment of Nucleic Acids to Agarose for Affinity Chromatography," *Biochemistry* 10:424.

Request to Amend Patent Request Or Any Other Filed Document, dated Oct. 10, 2002, filed in connection with Australian Patent Application No. 632857.

*Hoffman–La Roche, Inc.* v. *Promega Corporation*, 323 F.3d 1354, 66 U.S.P.Q.2d 1385, Mar. 21, 2003.

Reply dated Aug. 29, 2003 to the European Patent Office in response to submissions of Opponents II and III regarding EP Patent No. 0 258 017.

Submission dated Feb. 12, 2003 to the European Patent Office in response to Proprietor's Grounds of Appeal regarding European Patent Application No. 87307433.0–2106/0258017.

Order re *Hoffman–La Roche, Inc., et al.* v. *Promega Corp.*, USDC, N. D. Cal., Case No. 93–1748 VRW filed on May 13, 2004 executed by J. Vaughn R. Walker.

Decision of the Technical Board of Appeal 3.3.8 of Oct. 24, 2003, Case No. T 1080/–1–3.3.8, European Patent Office dated Feb. 20, 2004 and accompanying letters.

Declaration of Alexander Grigorevich Slyusarenko executed on May 24, 1994.

*Hoffman–LaRoche* v. *Promega* Trial Feb. 9, 1999 vol. 6, Excerpt from Stoffel Testimony, pp. 1033–1147.

Protest Letter dated Feb. 11, 2004 with attachments.

Communication regarding errors in Figures by Doug Petry, Dec. 21, 1999.

Dr. Rein's notebook pages (PR29185–PR291831).

"Summary of Attempts to Reproduce the Prior Art", table, p. 8 from Roche re–examination record.

Autoradiogram of the 28 hour exposure results of Dr. Mosbaugh in situ activity gel analysis on active fractions off the column (i.e., DNA–Sepharose) run by Dr. Rein as part of prep "4a".

Martin, R. et al., "A Method for determining the Sedimentation Behavior of Enzymes: Application to Protein Mixtures," J. of Biol. Chem. 236(5):1372–1379 (1961).

Sutherland, B. and Chamberlin, M., "Deoxyribonucleic Acid Photoreactivating Enzyme from *Escherichia coli*," J. Biol. Chem. (1972).

Submission by counsel for Roche in Europe to the EPO ("Appendix E"), "Description of the Reproduction of Edgar (03) and Brief Discussion of the Results," 3 pages.

Dr. Gelfand's email dated Oct. 4, 1991 (X012347).

Notebook page for a phosphocellulose experiment, showing graph entitled "P–1 Phosphocellulose Chromatography of Taq DNA Pol".

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–3 are cancelled.

New claim 4 is added and determined to be patentable.

*4. The polymerase of claim 3 wherein the recombinant organism transformed with a vector that codes for the expression of Thermus aquaticus DNA polymerase is E. coli.*

\* \* \* \* \*